United States Patent
Yamamoto

(10) Patent No.: US 11,426,052 B2
(45) Date of Patent: Aug. 30, 2022

(54) ENDOSCOPIC SYSTEM

(71) Applicant: Olympus Corporation, Hachioji (JP)

(72) Inventor: Naoki Yamamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 883 days.

(21) Appl. No.: 16/214,247

(22) Filed: Dec. 10, 2018

(65) Prior Publication Data

US 2019/0104921 A1 Apr. 11, 2019

Related U.S. Application Data

(63) Continuation of application No. PCT/JP2017/013938, filed on Apr. 3, 2017.

(30) Foreign Application Priority Data

Jun. 21, 2016 (JP) .............................. JP2016-122747

(51) Int. Cl.
*A61B 1/00* (2006.01)
*A61B 1/045* (2006.01)
(Continued)

(52) U.S. Cl.
CPC ............ *A61B 1/00009* (2013.01); *A61B 1/00* (2013.01); *A61B 1/00013* (2013.01); *A61B 1/04* (2013.01);
(Continued)

(58) Field of Classification Search
CPC ... A61B 1/00009; A61B 1/00; A61B 1/00013; A61B 1/04; A61B 1/045; A61B 1/00006;
(Continued)

(56) References Cited

U.S. PATENT DOCUMENTS

2001/0012053 A1* 8/2001 Nakamura ......... A61B 1/00193 348/45
2010/0208046 A1* 8/2010 Takahashi .......... A61B 1/00193 348/E7.085

(Continued)

FOREIGN PATENT DOCUMENTS

JP 2004-112111 4/2004
JP 2005-334462 12/2005
(Continued)

OTHER PUBLICATIONS

English machine translation JP-2014228851-A (Year: 2014).*
(Continued)

*Primary Examiner* — Timothy J Neal
(74) *Attorney, Agent, or Firm* — Scully, Scott, Murphy & Presser, P.C.

(57) ABSTRACT

An endoscopic system includes a left optical system having a first focal position, a right optical system having a second focal position that is different from the first focal position. An image capturing device generates a first image and a second image respectively from images of a subject that are obtained by the left optical system and the right optical system. A display device displays the first image or the second image. A proper image determiner determines the magnitude relationship between the position of the subject in a predetermined area displayed on the display device and at least one threshold value Th is established between the first focal position and the second focal position. A video signal processor switches to the first image or the second image depending on a determined result from the proper image determiner and displays the image on the display device.

21 Claims, 14 Drawing Sheets

(51) Int. Cl.
*G02B 23/24* (2006.01)
*A61B 90/00* (2016.01)
*A61B 1/04* (2006.01)
*A61B 1/06* (2006.01)
*H04N 5/225* (2006.01)

(52) U.S. Cl.
CPC .......... *A61B 1/045* (2013.01); *A61B 90/361* (2016.02); *G02B 23/243* (2013.01); *G02B 23/2415* (2013.01); *G02B 23/2461* (2013.01); *A61B 1/0005* (2013.01); *A61B 1/00006* (2013.01); *A61B 1/00096* (2013.01); *A61B 1/00188* (2013.01); *A61B 1/06* (2013.01); *G02B 23/2484* (2013.01); *H04N 2005/2255* (2013.01)

(58) Field of Classification Search
CPC .............. A61B 1/0005; A61B 1/00096; A61B 1/00188; A61B 1/06; A61B 1/00089; A61B 1/00193; A61B 5/6886; A61B 90/361; G02B 23/2415; G02B 23/243; G02B 23/2461; G02B 23/2484; G02B 30/22; H04N 2005/2255; H04N 13/239
See application file for complete search history.

(56) References Cited

U.S. PATENT DOCUMENTS

2014/0267626 A1* 9/2014 Lilagan ............ H04N 5/232125
            348/46
2018/0067296 A1* 3/2018 Sugie ............... H04N 5/232127

FOREIGN PATENT DOCUMENTS

| JP | 2006-280425 | | 10/2006 |
| JP | 2012-194352 | | 10/2012 |
| JP | 2013105078 A | * | 5/2013 |
| JP | 2014-228851 | | 12/2014 |
| JP | 2014228851 A | * | 12/2014 |

OTHER PUBLICATIONS

English machine translation JP-2013105078-A (Year: 2013).*
International Search Report and Written Opinion from corresponding International Application No. PCT/JP2017/013938, dated Jul. 4, 2017.

* cited by examiner

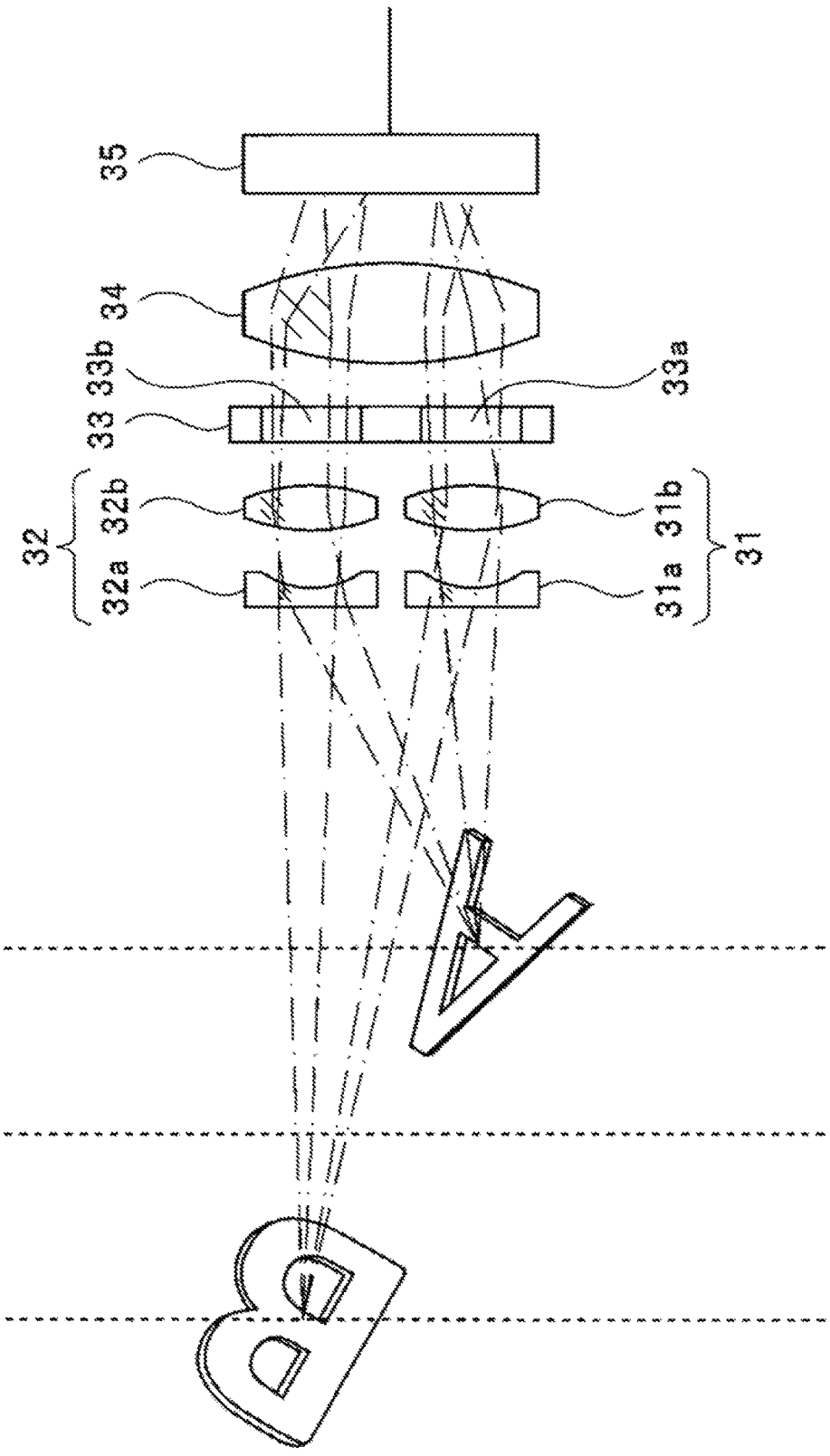

ENDOSCOPIC SYSTEM

CROSS-REFERENCE TO RELATED APPLICATIONS

This application is a continuation application of PCT Application No. PCT/JP2017/013938 filed on Apr. 3, 2017, which in turn claim priority to the Japanese Patent Application No. 2016-122747 filed on Jun. 21, 2016 in Japan which is hereby incorporated by reference in its entirety.

TECHNICAL FIELD

The technology disclosed herein relates to an endoscopic system, and more particularly to an endoscopic system for acquiring images from different optical paths.

DESCRIPTION OF THE RELATED ART

Endoscopes have widely been used in the medical field and the industrial field, etc. Endoscopic systems generally include an endoscope for capturing an image of a subject in a body, a video processor for generating an observational image of the subject whose image has been captured by the endoscope. And a monitor displays the observational image generated by the video processor. Particularly, industrial endoscopes are widely used to observe and inspect internal flaws and corrosions, etc. in boilers, turbines, engines, chemical plants, and so on.

Industrial endoscopes in recent years allow a stereo optical adapter for capturing images of a subject from different viewpoints to be mounted on the distal end of an endoscope, and endoscopes for stereo measurement capable of measuring various spatial characteristics of a subject based on the principle of triangulation have been in use.

Conventional endoscopes for stereo measurement operate by projecting two images defined as respective left and right images with a parallax onto different areas on the image capturing surface of a single image capturing device. And, if a live image is to be observed, performing a binocular display mode that displays an image including both the two left and right images. Since the two images are displayed on a display, in this case, the individual images are displayed in small sizes, resulting in a reduction in observing capability. In order to increase observing capability, therefore, there has been proposed an endoscope for performing a monocular display mode that displays an image including only one of two left and right images if a live image is to be observed. There has also been proposed for increased observing capability an endoscope for performing a monocular display mode by projecting images from two time-division-switched optical paths onto a common area of the image capturing surface of a single image capturing device.

Furthermore, Japanese Patent Laid-Open No. 2014-228851, for example, has proposed for increased observing capability of an endoscope that increases a field of depth by combining images captured by a plurality of optical systems having different focal positions.

Moreover, Japanese Patent Laid-Open No. 2006-280425, for example, has proposed for increased observing capability of an endoscope that includes an actuating mechanism disposed in a distal-end portion thereof for actuating a focus-adjusting lens to perform automatic focusing on an observational region.

However, the endoscope disclosed in Japanese Patent Laid-Open No. 2014-228851 requires a lot of processing time, imposing a large burden on a controller such as a CPU or the like, in order to combine the images captured at the different focal positions. Since the endoscope needs to display captured images in real time, it is difficult to apply the image combining process that requires a lot of processing time.

An endoscope that includes an automatic focusing mechanism, as with the endoscope disclosed in Japanese Patent Laid-Open No. 2006-280425, has a large-diameter distal-end portion because it incorporates therein an actuating mechanism for actuating a lens. Depending on an object to be observed by the endoscope, the endoscope needs to be inserted from its insertion portion into a small slit in the object. The large-diameter distal-end portion tends to impair the ability of the endoscope to reach and observe details in the object to be observed.

BRIEF SUMMARY OF EMBODIMENTS

The technology disclosed herein is directed to an endoscopic system that is capable of displaying better-focused images without causing an increase in the burden on a CPU and making a distal-end portion larger in diameter.

According to an aspect of the present disclosure, there is provided an endoscopic system including a first optical system having a first focal position. A second optical system has a second focal position that is different from the first focal position of the first optical system. An image capturing device generates a first image and a second image respectively from images of a subject that are obtained by the first optical system and the second optical system. A display device is used to display the first image or the second image. A proper image determiner is configured to determine magnitude relationship between a position of the subject in a predetermined area displayed on the display device and at least one threshold value that is established between the first focal position and the second focal position. A display controller is configured to switch to the first image or the second image depending on a determined result from the proper image determiner and to display the first image or the second image on the display device.

Another aspect of the disclosed technology is directed to an endoscopic system comprises a first optical system having a first focal position is configured to form a first image of a subject. A second optical system having a second focal position that is different from the first focal position and is configured to form a second image the subject. Each of the first optical system and the second optical system includes a parallax with respect to one another. An image capturing device has an image capturing surface and is configured to capture the respective first image and the second image. A display device displays the first image or the second image being captured by the image capturing device. A proper image determiner is configured to compare a position of the subject in a part of an area displayed on the display device with at least one threshold value being established between the first focal position and the second focal position and is configured to output a determined result. A display controller is configured to switch to the first image or the second image based on the determined result and controls the display device for displaying the first image or the second image. A range finder is configured to measure a distance up to the position of the subject in the part of the area by performing stereo measurement on the first image and the second image and outputting a measured distance.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 4 is a view illustrating the relationship between the focal positions of a left optical system and a right optical system and a threshold value.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

First Embodiment

Figure 1:
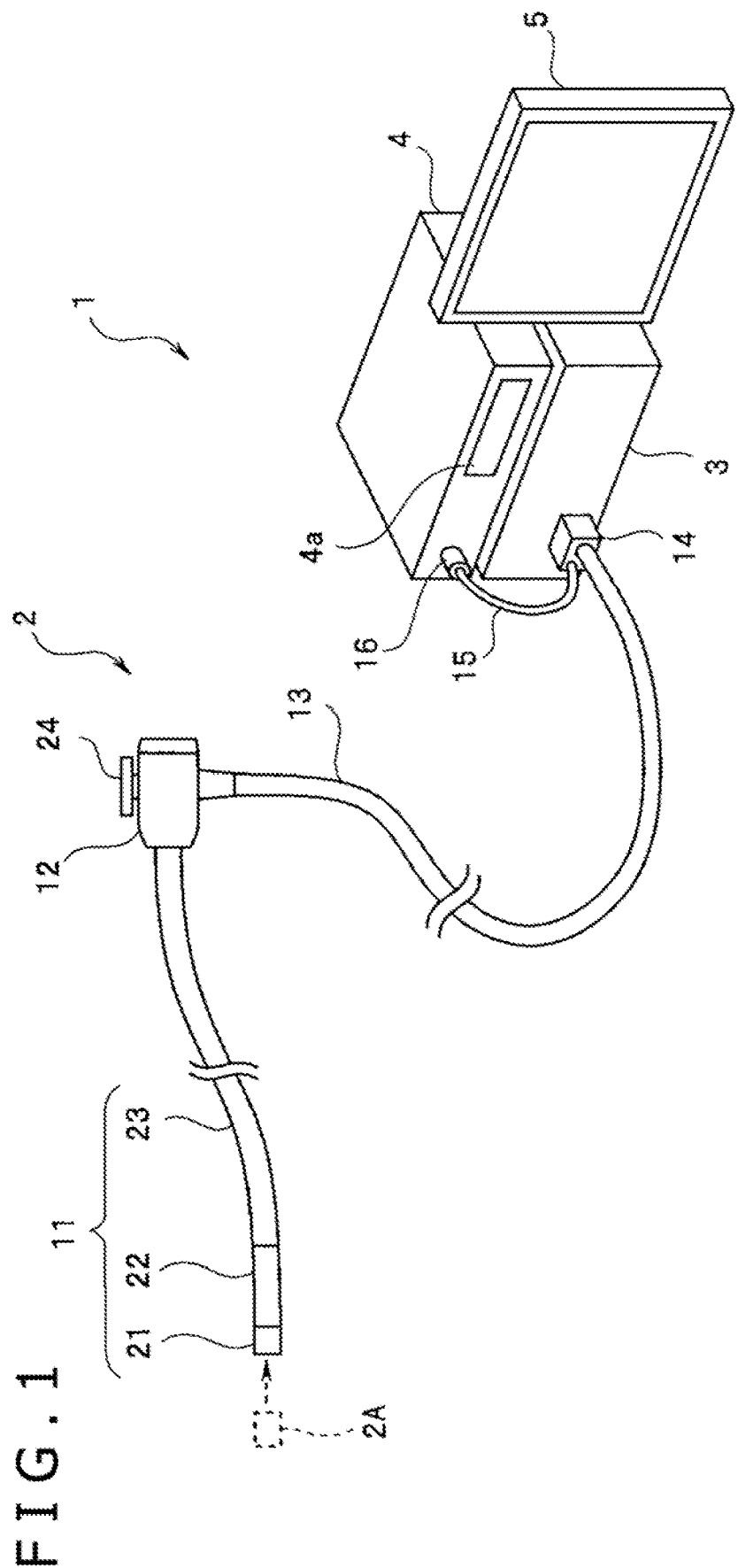
FIG. 1 is a configuration view illustrating a configuration of an endoscopic system according to a first embodiment.

FIG. 1 is a configuration view illustrating a configuration of an endoscopic system according to a first embodiment. As illustrated in FIG. 1, the endoscopic system, denoted by 1, according to the present embodiment includes an endoscope 2, a light source device 3 to which the endoscope 2 is connected, a main device 4 including a camera control unit (hereinafter referred to as "CCU"), etc., and a display 5. The display 5 is defined as a display device that displays information in pictorial form and the likes.

The endoscope 2 is an electronic endoscope having an insertion portion 11 that is slender and flexible, a manipulator 12 connected to the proximal end of the insertion portion 11, and a universal cable 13 extending from the manipulator 12. An optical adapter 2A can be mounted on the distal end of the insertion portion 11.

A connector 14 that is disposed on the distal end of the universal cable 13 extending from the manipulator 12 can be detachably mounted on the light source device 3. A signal cable 15 extends from the connector 14. A connector 16 disposed on an end of the signal cable 15 can be detachably mounted on the main device 4.

The insertion portion 11 of the endoscope 2 has a hard distal-end portion 21 on its distal end, a bendable portion 22 disposed adjacent to the distal-end portion 21, and an elongate flexible tube portion 23 connected to the proximal end side of the bendable portion 22. The user of the endoscopic system 1 can bend the bendable portion 22 by operating a bending knob 24 disposed on the manipulator 12.

Figure 2:
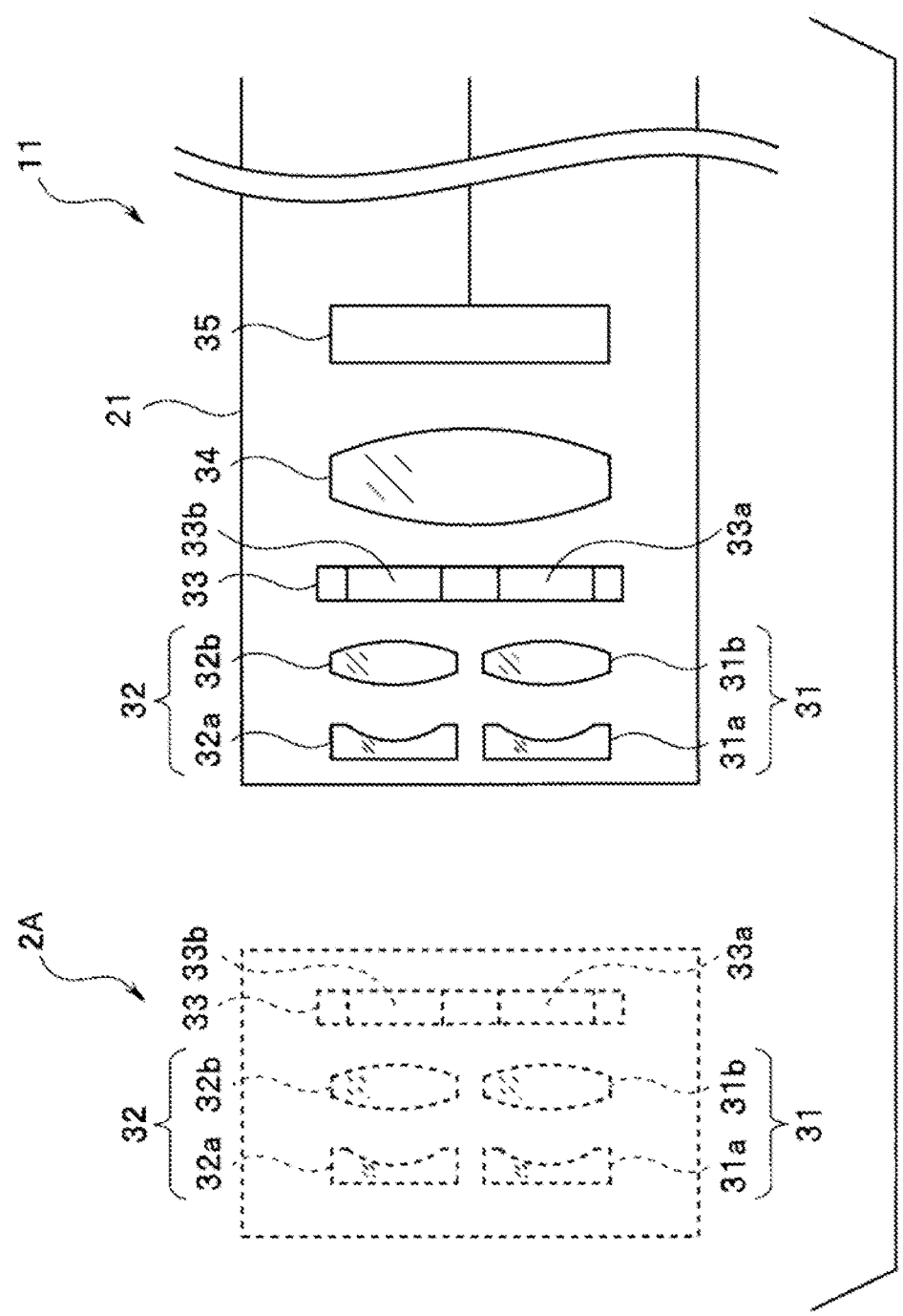
FIG. 2 is a view illustrating a configuration of an optical system in the distal-end portion of an insertion portion.

The distal-end portion 21 houses therein an image capturing device 35 (see FIG. 2). A captured image signal that is obtained by the image capturing device 35 is supplied through signal lines inserted in the insertion portion 11, the manipulator 12, the universal cable 13, and the signal cable 15 to the main device 4.

The light source device 3 includes a light source such as a lamp or the like for producing illuminating light that is applied to the proximal-end face of an optical fiber, not shown, inserted in the universal cable 13 and the insertion portion 11 and that is emitted from the distal end of the insertion portion 11 to illuminate an examinee.

The main device 4 includes, in addition to the CCU, a controller for controlling the endoscopic system 1 in its entirety. The main device 4 includes a central processing unit (CPU), not shown, a ROM, a RAM, and so on, and the user can perform various operations on an operation panel 4a thereof. In order to perform functions depending on user's operations, the main device 4 executes programs according to the functions. The main device 4 receives a captured image signal from the endoscope 2 and outputs an image signal representing endoscope images which are examinee images generated by the CCU to the display 5, which displays the endoscope images.

FIG. 2 is a view illustrating a configuration of an optical system in the distal end portion of the insertion portion. The distal-end portion 21 of the insertion portion 11 includes a left optical system 31, a right optical system 32, a light shield 33, a focusing optical system 34, and the image capturing device 35, as illustrated in FIG. 2.

The left optical system 31 includes lenses 31a and 31b. The right optical system 32 includes lenses 32a and 32b. The left optical system 31 and the right optical system 32 are designed to have different focal positions, respectively. According to the present embodiment, the left optical system 31 as a first optical system is designed to have its focal position on a near point side, or at a first focal position, whereas the right optical system 32 is designed to have its focal position on a far point side, or at a second focal position. Specifically, the right optical system 32 as a second optical system has the second focal position that is different from the first focal position of the left optical system 31 as the first optical system. The left optical system 31 and the right optical system 32 are designed to have respective images focused on an identical area of the single image capturing device 35. Specifically, the image capturing device 35 generates a first image and a second image from images of a subject that are obtained by the left optical system 31 and the right optical system 32, respectively.

Although the focal position of the left optical system 31 is designed to be on the near point side and the focal position of the right optical system 32 on the far point side, the focal position of the left optical system 31 may be designed to be on the far point side and the focal position of the right optical system 32 on the near point side.

Since the optical systems used in the endoscopic system 1 are small optical systems, the focal position of the left optical system 31 and the focal position of the right optical system 32 may be different from each other due to a variation in the manufacturing process therefor. Therefore, a left optical system 31 and a right optical system 32 which have different focal positions due to variations in the manufacturing process may be applied to the endoscopic system 1 though the focal positions of the left optical system 31 and the right optical system 32 that are designed to be different from each other are illustrated in the present embodiment.

The light shield 33 as an optical path switcher has two openings 33a and 33b disposed in alignment with two optical paths of the left optical system 31 and the right optical system 32. The light shield 33 has shield members, not shown, for alternately shielding the openings 33a and 33b on a time-division basis.

The focusing optical system 34 is arranged to focus light that has passed through the two optical paths of the left optical system 31 and the right optical system 32 on a common area of the image capturing device 35. The image capturing device 35 is disposed in the focal position of the focusing optical system 34, and captures images from the two optical paths of the left optical system 31 and the right optical system 32, which images have been focused with a time difference as the optical paths are alternately shielded by the light shield 33 on a time-division basis. A captured image signal from the image capturing device 35 is supplied to the main device 4.

The endoscopic system 1 according to the present embodiment is thus an apparatus capable of acquiring a plurality of images with a time difference by time-division-switching the two optical paths of the left optical system 31 and the right optical system 32.

In case the optical adapter 2A is mounted on the distal-end portion 21, the optical adapter 2A may have the left optical system 31, the right optical system 32, and the light shield 33. In this case, the distal-end portion 21 of the insertion portion 11 may have only the focusing optical system 34 and the image capturing device 35.

Figure 3:
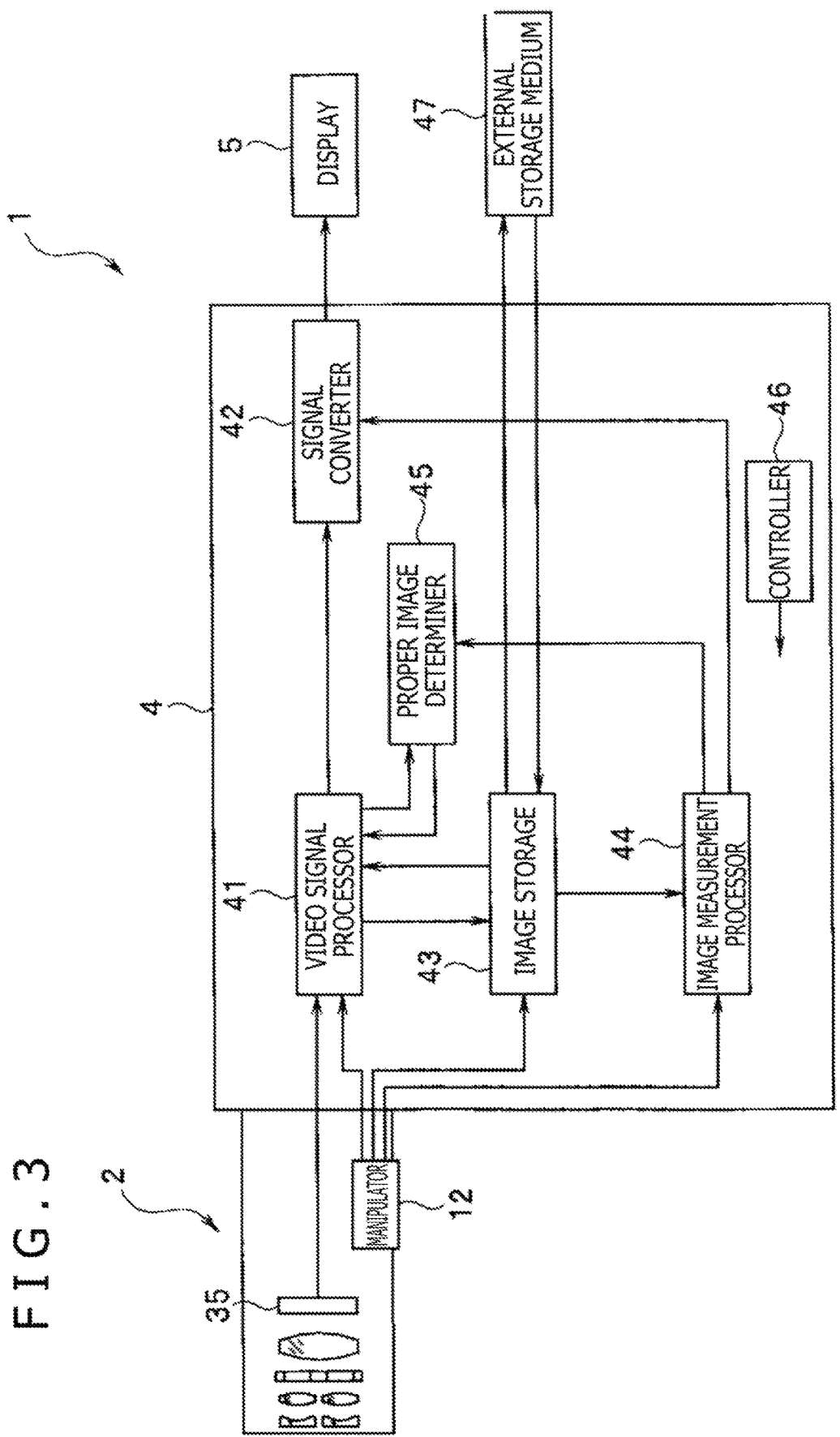
FIG. 3 is a block diagram showing a detailed configuration of the endoscopic system.

FIG. 3 is a block diagram showing a detailed configuration of the main device 4 of the endoscopic system 1. As illustrated in FIG. 3, the main device 4 includes a video signal processor 41 as a CCU, a signal converter 42, an image storage 43, an image measurement processor 44, a proper image determiner 45, and a controller 46. To the main device 4, there is removably connected an external storage medium 47 that can store endoscope images and various pieces of information therein. The video signal processor 41, the signal converter 42, the image storage 43, the image measurement processor 44, and proper image determiner 45 can be a part of a controller. The controller may be formed by one or more processors as a hardware. The one or more processors may be constructed as programmable device such as CPUs, FPGAs, or the like, or devices such as ASICs.

The video signal processor 41 performs a predetermined video processing sequence on a captured image signal input from the image capturing device 35, generates a video signal, and outputs the generated video signal to the signal converter 42 and the image storage 43.

The signal converter 42 generates a display video signal from the video signal output from the video signal processor 41, and outputs the generated display video signal to the display 5. Furthermore, the signal converter 42 may combine other image data such as of an operation screen image or the like with a display video signal, when necessary. Moreover, if measurement information is output from the image measurement processor 44, the signal converter 42 generates a video signal by combining the measurement information with a display video signal, and outputs the generated video signal to the display 5.

The image storage 43 stores therein a video signal output from the video signal processor 41 as a still image or moving image. Furthermore, if an image recording instruction is input from the manipulator 12, the image storage 43 reads a stored image and outputs the read image to the external storage medium 47 as controlled by the controller 46.

The image measurement processor 44 as a range finder performs a measuring process using still image data stored in the image storage 43. When a measuring point, e.g., a cursor to be described hereinafter, is established on the display screen of the display 5, the image measurement processor 44 acquires positional information of a corresponding point, which corresponds to the measuring point, on images with a parallax from the left optical system 31 and the right optical system 32, calculates three-dimensional coordinates of the measuring point based on the principle of triangulation, and measures the distance up to the measuring point. The image measurement processor 44 outputs the measured distance to the signal converter 42 and the proper image determiner 45.

The proper image determiner 45 determines whether the measured distance from the image measurement processor 44 is larger than a predetermined threshold value Th or not, and determines which one of the left and right images from the left optical system 31 and the right optical system 32 is focused better. More specifically, the proper image determiner 45 as a determiner determines the magnitude relationship between the position of a subject in a predetermined area displayed on the display 5 and at least one threshold value Th established between the focal position of the left optical system 31 and the focal position of the right optical system 32. The determined result from the proper image determiner 45 is input to the video signal processor 41.

Based on the determined result from the proper image determiner 45, the video signal processor 41 outputs a better-focused one of the left and right images from the left optical system 31 and the right optical system 32 to the signal converter 42. As described hereinbefore, the signal converter 42 generates an endoscope image by combining measurement information or the like with the image from the video signal processor 41, when necessary, and outputs the generated endoscope image to the display 5.

Figure 5A:
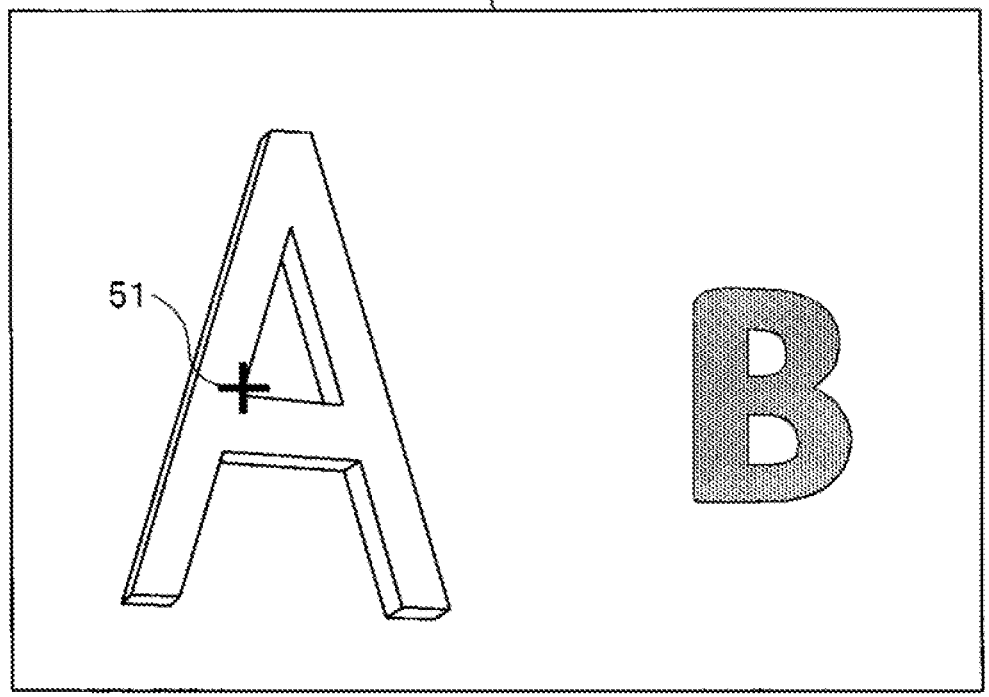
FIG. 5A is a diagram illustrating an example of a display screen of an image acquired by the left optical system.
Figure 5B:
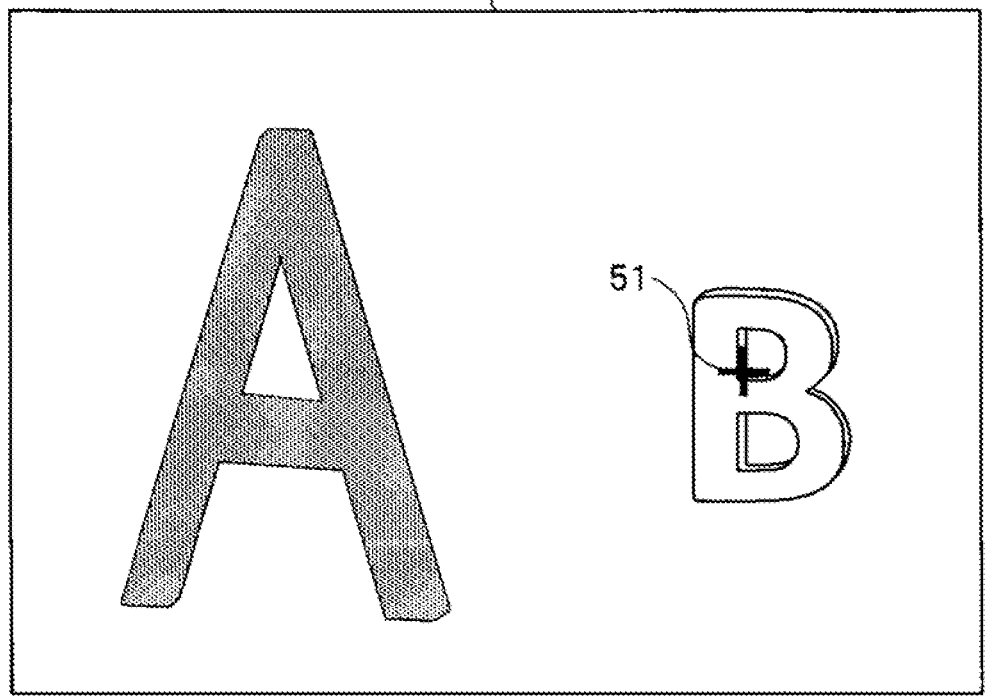
FIG. 5B is a diagram illustrating an example of a display screen of an image acquired by the right optical system.

FIG. 4 is a view illustrating the relationship between the focal positions of the left optical system and the right optical system and the threshold value, FIG. 5A is a diagram illustrating an example of a display screen of an image acquired by the left optical system, and FIG. 5B is a diagram illustrating an example of a display screen of an image acquired by the right optical system.

As illustrated in FIG. 4, the focal position of the left optical system 31 is a position close to a near point where an object "A" is placed. On the other hand, the focal position of the right optical system 32 is a position close to a far point where an object "B" is placed. The threshold value Th is established at an object distance intermediate between the best-focused position of the left optical system 31 and the best-focused position of the right optical system 32. Although the threshold value Th is established at a central position between the left and right focal positions, i.e., intermediate between the left and right best-focused positions, according to the present embodiment, the threshold value Th may not be established at the central position insofar as it lies somewhere between the left and right focal positions.

If the measured distance from the image measurement processor 44 is larger than the threshold value Th, then the proper image determiner 45 determines that, of the left and right images, the image generated from the right optical system 32 whose focal position is on the far point side is in focus. On the other hand, if the measured distance from the image measurement processor 44 is equal to or smaller than the threshold value Th, then the proper image determiner 45 determines that, of the left and right images, the image generated from the left optical system 31 whose focal position is on the near point side is in focus.

The left optical system 31 is focused on the object "A" and is not focused on the object "B." Therefore, as illustrated in FIG. 5A, an image where the object "A" is in focus and the object "B" is blurred is acquired from the left optical system 31.

On the other hand, the right optical system 32 is not focused on the object "A" and is focused on the object "B." Therefore, as illustrated in FIG. 5B, an image where the object "A" is blurred and the object "B" is in focus is acquired from the right optical system 32.

When the user establishes a cursor 51 as a measuring point on the display 5 using the manipulator 12, the image measurement processor 44 measures the distance up to an object on which the cursor 51 is established. The proper image determiner 45 determines a better-focused one of the left and right images by determining whether the measured distance from the image measurement processor 44 is larger than the threshold value Th. In the description hereinafter, a better-focused one of the left and right images will be referred to as a proper image. The proper image determiner 45 thus constitutes a determiner for determining which one of the focal position of the left optical system 31 and the focal position of the right optical system 32 the position of a subject in a predetermined area displayed on the display 5 is close to.

For example, if the cursor 51 is established in the vicinity of the object "A," then since the measured distance from the image measurement processor 44 is equal to or smaller than the threshold value Th, the proper image determiner 45 determines that the image acquired from the left optical system 31 is in better focus. Based on the determined result from the proper image determiner 45, the image signal processor 41 displays the image illustrated in FIG. 5A acquired from the left optical system 31 on the display 5.

On the other hand, if the cursor 51 is established in the vicinity of the object "B," then since the measured distance from the image measurement processor 44 is larger than the threshold value Th, the proper image determiner 45 determines that the image acquired from the right optical system 32 is in better focus. Based on the determined result from the proper image determiner 45, the image signal processor 41 displays the image illustrated in FIG. 5B acquired from the right optical system 32 on the display 5.

The video signal processor 41 thus constitutes a display controller for switching to the image obtained from the left optical system 31 or the image obtained from the right optical system 32 depending on the determined result from the proper image determiner 45, and displaying the image on the display 5. The display 5 displays an image, or a first image, acquired when the subject image obtained from the left optical system 31 is focused on an image capturing area of the image capturing device 35 or an image, or a second image, acquired when the subject image obtained from the right optical system 32 is focused on an image capturing area of the image capturing device 35.

Figure 6:
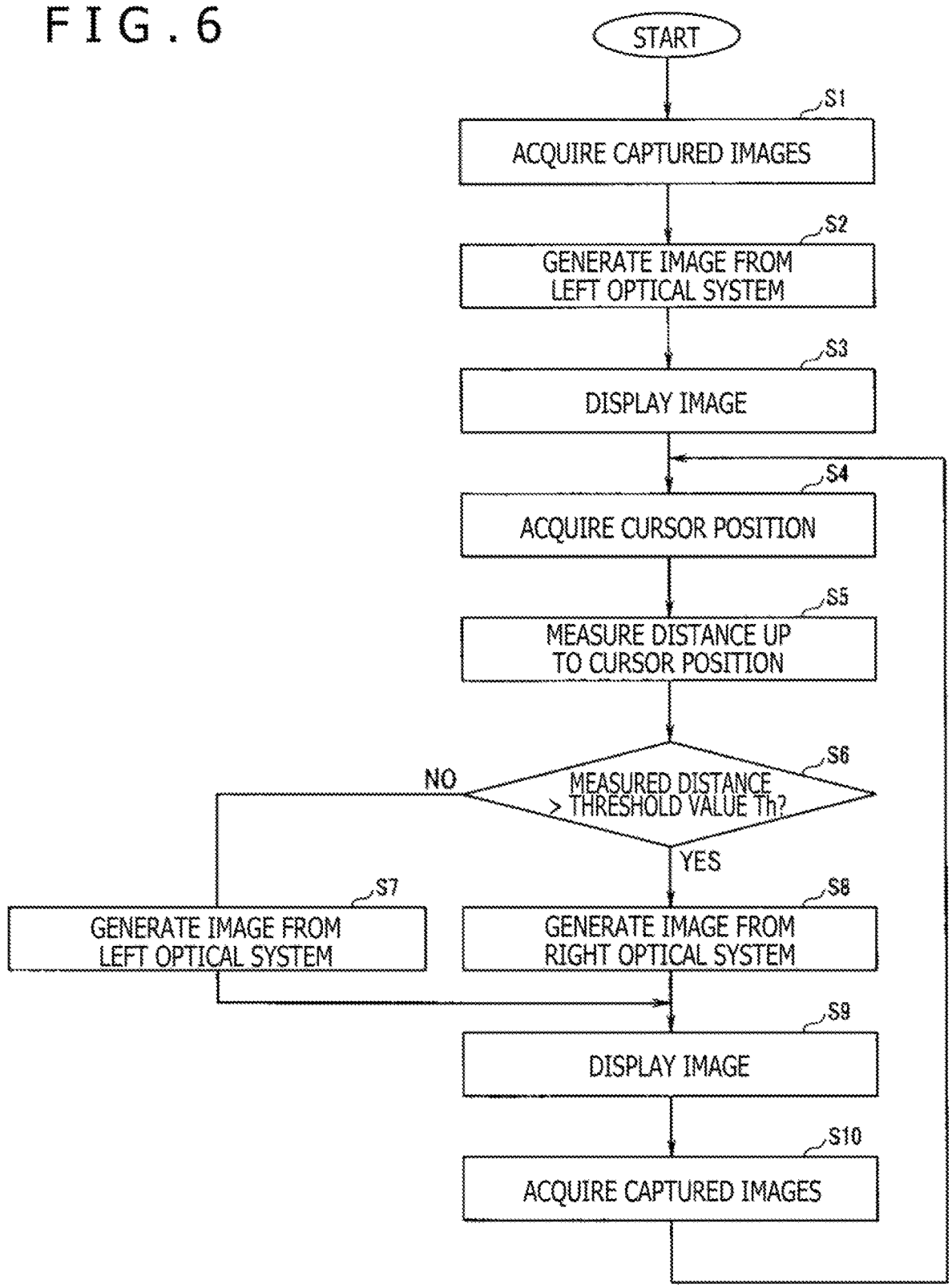
FIG. 6 is a flowchart illustrating an example of a display process for displaying a better-focused one of left and right images.

Next, a display process for displaying a better-focused one of the left and right images will be described hereinafter. FIG. 6 is a flowchart illustrating an example of the display process for displaying a better-focused one of the left and right images.

When the endoscopic system 1 is activated, captured images from the left optical system 31 and the right optical system 32 are acquired by switching between the two optical paths with the light shield 33 in step S1. Then, an image from the left optical system 31 is generated in step S2, and the generated image is displayed on the display 5 in step S3. In the processing of step S2, an image from an optical system set to a default setting, i.e., either one of the left optical system 31 and the right optical system 32, is generated. According to the present embodiment, the left optical system 31, for example, is set to a default setting, though the right optical system 32 may be set to a default setting.

Next, when the user sets the cursor 51 on the screen of the display 5 using the manipulator 12, a cursor position is acquired in step S4, and the distance up to the cursor position on the screen is measured according to stereo measurement in step S5.

According to the present embodiment, upon stereo measurement, since the focal positions of the left optical system 31 and the right optical system 32 are different from each other, the image from the left optical system 31 and the image from the right optical system 32 are different as to how they are blurred, resulting in a reduction in the accuracy of stereo matching. Therefore, after stereo measurement has been carried out once, a template image and an image in a search range are processed by a deconvolution process using PSF (point spread function) corresponding to object distance information, generating an image where one of the images is deblurred, and then stereo matching is performed on the generated image. Inasmuch as the resolutions of the left and right images are thus brought closely to each other, the accuracy of stereo matching is increased, so that a more accurate measured distance can be obtained.

Although one of the images is deblurred by the deconvolution process to equalize the resolutions of the left and right images, the present invention is not limited to such a process. Rather, the other image may be blurred by a convolution process.

Alternatively, for example, the image from the left optical system 31 may be deblurred and the image from the right optical system 32 may be blurred, so that the resolutions of the left and right images may be equalized by the combination of the deblurring and blurring processes. The resolutions of the left and right images may be equalized by any processes other than the above image processing processes.

Next, it is determined whether the measured distance is larger than the threshold value Th or not in step S6. If it is determined that the measured distance is not larger than the threshold value Th (step S6: NO), i.e., if it is determined that the measured distance is equal to or smaller than the threshold value Th, then an image from the left optical system 31 is generated in step S7, and the generated image is displayed on the display 5 in step S9. On the other hand, if it is determined that the measured distance is larger than the threshold value Th (step S6: YES), then an image from the right optical system 32 is generated in step S8, and the generated image is displayed on the display 5 in step S9. After the processing of step S9 has been carried out, captured images from the left optical system 31 and the right optical system 32 are acquired by switching between the two optical paths with the light shield 33 in step S10. Control then goes back to step S4, from which the same process is repeated.

According to the processing sequence described hereinbefore, the endoscopic system 1 is not required to combine the acquired two images and to incorporate a focus adjusting mechanism in the distal-end portion 21. Of the images acquired from the left optical system 31 and the right optical system 32, an image that is in better focus in an area that the user is interested in can automatically be displayed on the display 5, so that the endoscopic system 1 can have a better observing capability. As the endoscopic system 1 does not need to combine the two acquired images, the burden on the CPU is not increased. Furthermore, since the endoscopic system 1 has no focus adjusting mechanism incorporated in the distal-end portion 21, the distal-end portion 21 is not made larger in diameter.

The endoscopic system 1 according to the present embodiment is thus capable of displaying better-focused images without causing an increase in the burden on the CPU and making the distal-end portion 21 larger in diameter.

While the endoscopic system 1 has a display mode for automatically switching to one of the right image and the left image depending on the measured distance and displaying the image according to the present embodiment, the endoscopic system 1 may also have another display mode for displaying the right image at all times or displaying the left image at all times, for example, and the user may select each of the display modes using the manipulator 12 or the like.

Modification 1

Next, modification 1 of the first embodiment will be described hereinafter. According to the embodiment described hereinbefore, the distance up to an object is measured by stereo measurement. However, the present invention is not limited to such stereo measurement. The distance up to an object may be measured using another range finding process such as a TOF (time of flight) process, a triangulation process for applying a laser spot to a subject, or the like.

According to the embodiment described hereinbefore, a range finding point is a single point where the cursor 51 is established. However, the present invention is not limited to a single range finding point. Rather, the distances up to a plurality of points may be measured, and a proper image may be determined depending on the measured distances. Alternatively, the present invention is not limited to measuring distances up to certain points. The distance up to an entire image or a certain demarcated area may be measured.

Furthermore, according to the embodiment described hereinbefore, a proper image is determined depending on a measured distance. However, the present invention is not limited to such a determining process. Rather, a proper image may be determined depending on the luminance of an image or an area feature quantity.

For determining a proper image depending on the luminance of an image, the amount of light falling on the image capturing device 35 is determined. If the amount of light falling on the image capturing device 35 is larger than a predetermined threshold value, then the object is estimated to be near, and if the amount of light falling on the image capturing device 35 is equal to or smaller than the predetermined threshold value, then the object is estimated to be far. If the object is estimated to be near, the proper image determiner 45 determines the image from the left optical system 31 whose focal position is on the near point side to be a proper image, and if the object is estimated to be far, the proper image determiner 45 determines the image from the right optical system 32 whose focal position is on the far point side to be a proper image.

For determining a proper image depending on an area feature quantity, edges of given objects in the left and right images are detected. If an image is blurred, the contrast at the boundary of the edge is small, and if an image is not blurred, the contrast at the boundary of the edge is large. Therefore, if the contrast at the boundary of the edge is small, then the image is estimated to be blurred, and if the contrast at the boundary of the edge is large, then the image is estimated to be not blurred. The proper image determiner 45 determines an image where the contrast at the boundary of the edge is large, of the left and right images, as a proper image.

According to the present embodiment, an edge of a certain object is detected to determine a position where contrast is to be calculated. However, according to a simplified process, contrast may be calculated in a predetermined area such as a central area of the left image and the right image.

According to the present embodiment, the contrast at an edge is used as an area feature quantity. However, other indexes including the dispersion of pixel values in a predetermined area and a feature quantity based on a co-occurrence matrix may be used.

Modification 2

Next, modification 2 of the first embodiment will be described hereinafter.

According to the embodiment described hereinbefore, the displayed image is switched each time depending on the measured distance. If the measured distance is not stable in the vicinity of the threshold value Th, the image displayed on the display screen is switched frequently to an annoying and troublesome extent. Therefore, the displayed image may be switched only if the measured distance is larger than the threshold value Th successively a plurality of times, i.e., successively N times where N is an integer of 2 or greater, or if the measured distance is equal to or smaller than the threshold value Th successively a plurality of times. For example, if it is determined that the measured distance is larger than the threshold value Th successively a plurality of times while the image from the left optical system 31 whose focal position is on the near point side is being displayed, the displayed image is switched to the image from the right optical system 32 whose focal position is on the far point side.

As a result, the displayed image is prevented from being switched frequently if the measured distance is not stable in the vicinity of the threshold value Th, so that the endoscopic system 1 can have a better observing capability.

Furthermore, according to the embodiment described hereinbefore, a proper image is determined based on the threshold value Th to switch the displayed image. However, a proper image may be determined using two threshold values Th1 and Th2 to switch the displayed image.

Figure 7:
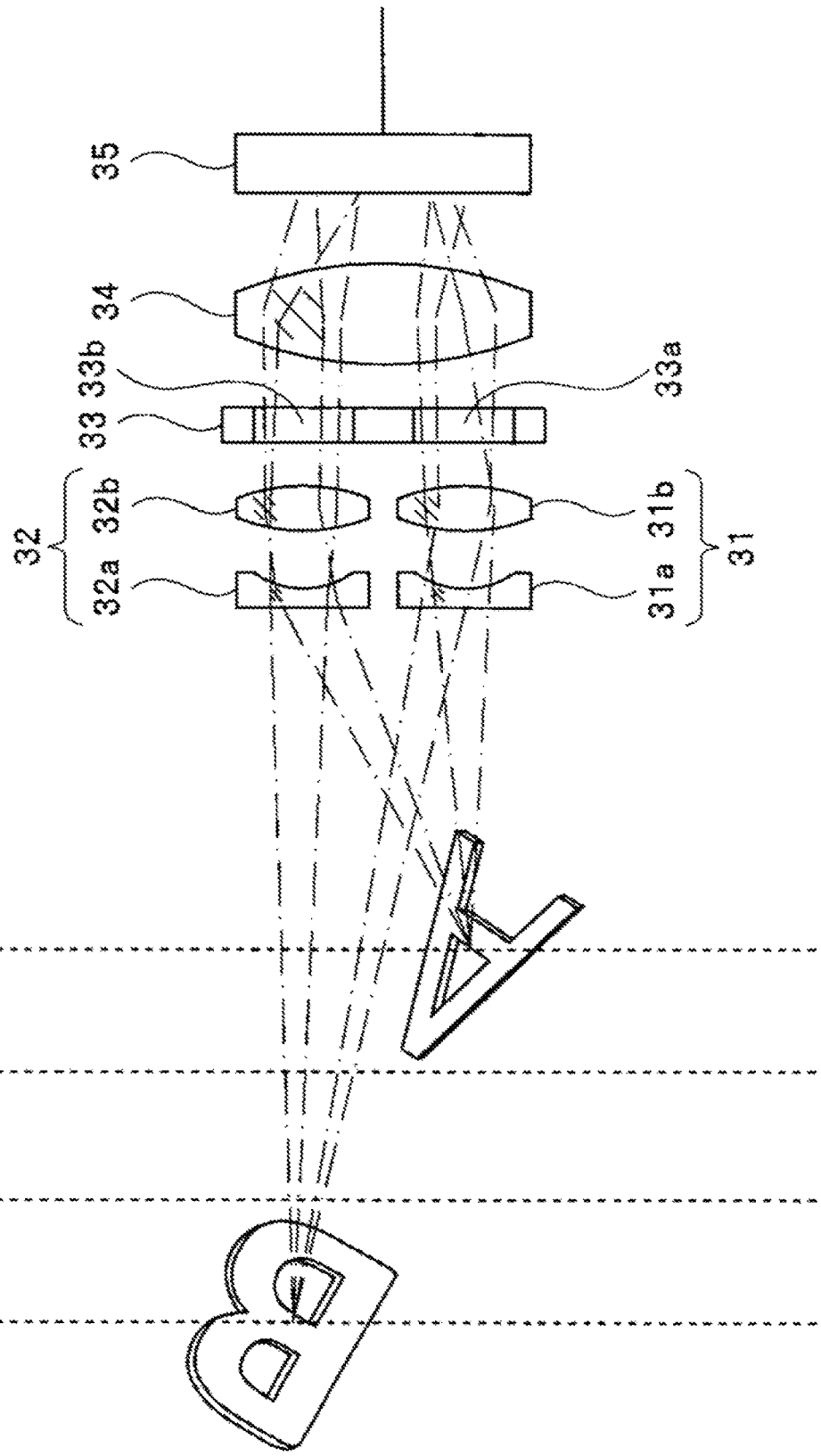
FIG. 7 is a view illustrating the relationship between the focal positions of the left optical system and the right optical system and threshold values.

FIG. 7 is a view illustrating the relationship between the focal positions of the left optical system and the right optical system and threshold values. As illustrated in FIG. 7, a threshold value Th1 is set on the side of the focal position of the right optical system, and a threshold value Th2 is set on the side of the focal position of the left optical system. The two threshold values Th1 and Th2 are related as the threshold value Th1>the threshold value Th2. Such a hysteresis may be introduced to prevent the displayed image from being switched frequently if the measured distance is unstable.

First, the image from the left optical system is displayed according to a default setting. If the proper image determiner 45 determines that the measured distance is equal to or smaller than the threshold value Th1 while the image from the left optical system 31 is being displayed, then the proper image determiner 45 determines that the image from the left optical system 31 is a proper image. On the other hand, if the proper image determiner 45 determines that the measured distance is larger than the threshold value Th1 while the image from the left optical system 31 is being displayed, then the proper image determiner 45 determines that the image from the right optical system 32 is a proper image.

If the proper image determiner 45 determines that the measured distance is equal to or larger than the threshold value Th2 while the image from the right optical system 32 is being displayed, then the proper image determiner 45 determines that the image from the right optical system 32 is a proper image. On the other hand, if the proper image determiner 45 determines that the measured distance is smaller than the threshold value Th1 while the image from the right optical system 32 is being displayed, then the proper image determiner 45 determines that the image from the left optical system 31 is a proper image.

Figure 8:
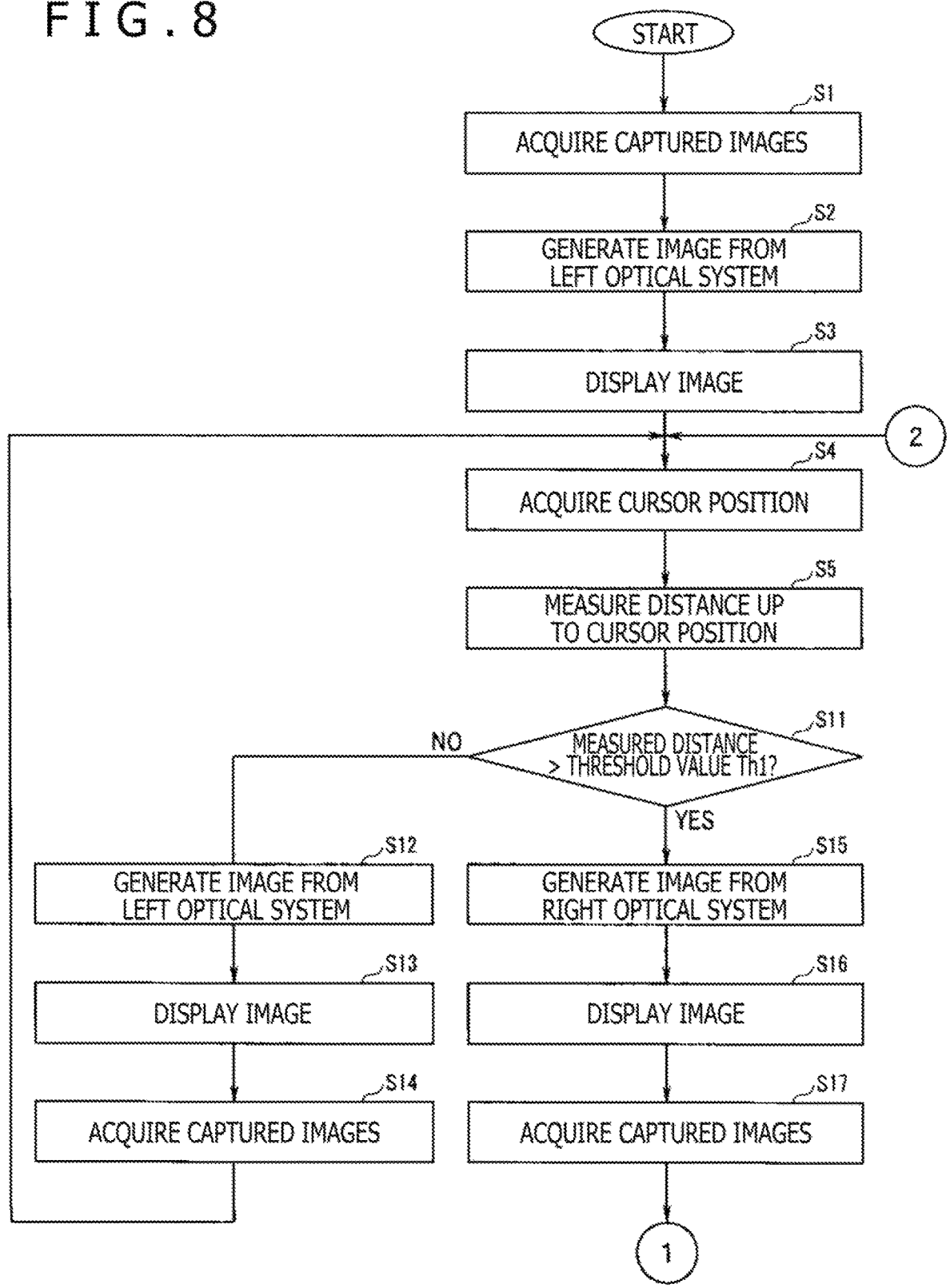
FIG. 8 is a flowchart illustrating an example of a display process for displaying a better-focused one of left and right images.
Figure 9:
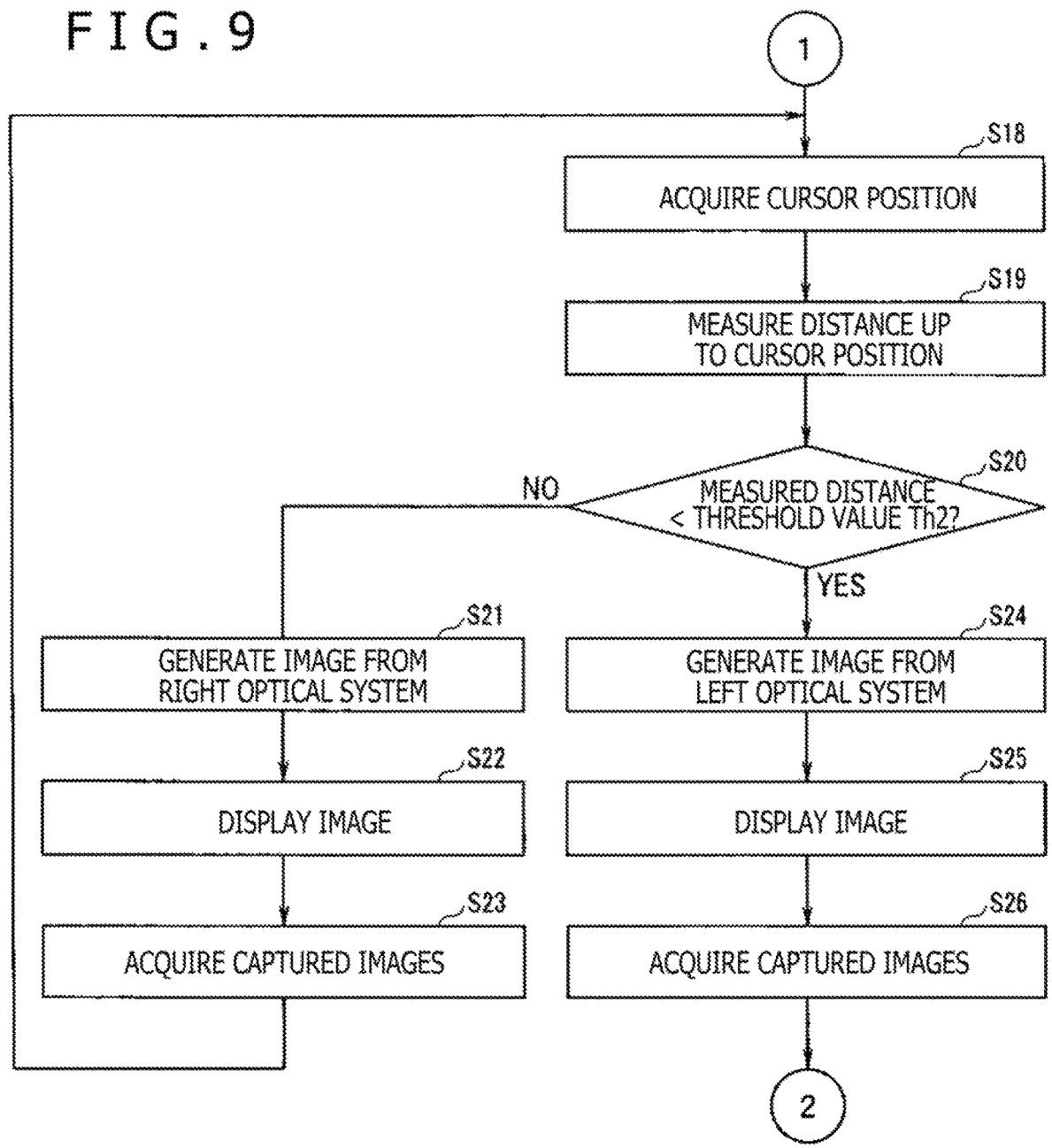
FIG. 9 is a flowchart illustrating the example of the display process for displaying a better-focused one of left and right images.

A display process for displaying a better-focused one of the left and right images will be described hereinafter. FIGS. 8 and 9 are flowcharts illustrating an example of the display process for displaying a better-focused one of left and right images. The processing steps illustrated in FIG. 8 that are identical to those illustrated in FIG. 6 are denoted by identical numeral references.

When the endoscopic system 1 is activated, captured images from the left optical system 31 and the right optical system 32 are acquired by switching between the two optical paths with the light shield 33 in step S1. Then, an image from the left optical system 31 is generated in step S2, and the generated image is displayed on the display 5 in step S3. In the processing of step S2, an image from an optical system set to a default setting, i.e., either one of the left optical system 31 and the right optical system 32, is generated. According to the present modification, the left optical system 31, for example, is set to a default setting, though the right optical system 32 may be set to a default setting.

Next, when the user sets the cursor 51 on the screen of the display 5 using the manipulator 12, a cursor position is acquired in step S4, and the distance up to the cursor position on the screen is measured according to stereo measurement in step S5.

After the distance up to the cursor position has been measured in step S5, it is determined whether the measured distance is larger than the threshold value Th1 or not in step S11. If it is determined that the measured distance is not larger than the threshold value Th1, i.e., if it is determined that the measured distance is equal to or smaller than the threshold value Th1 (step S11: NO), then an image from the left optical system 31 is generated in step S12, and the generated image is displayed on the display 5 in step S13. The two optical paths are switched by the light shield 33, and captured images from the left optical system 31 and the right optical system 32 are acquired in step S14, after which control goes back to the processing of step S4.

On the other hand, if it is determined that the measured distance is larger than the threshold value Th1 (step S11: YES), then an image from the right optical system 32 is generated in step S15, and the generated image is displayed on the display 5 in step S16. The two optical paths are switched by the light shield 33, and captured images from the left optical system 31 and the right optical system 32 are acquired in step S17, after which control goes to the processing sequence of FIG. 9.

After the captured images have been acquired in step S17, control goes to the processing sequence of FIG. 9. A cursor position is acquired in step S18, and the distance up to the cursor position is measured in step S19. Next, it is determined whether the measured distance is smaller than the threshold value Th2 or not in step S20. If it is determined that the measured distance is not smaller than the threshold value Th2 (step S20: NO), i.e., the measured distance is equal to or larger than the threshold value Th2, then an image from the right optical system 32 is generated in step S21, and the generated image is displayed on the display 5 in step S22. The two optical paths are switched by the light shield 33, and captured images from the left optical system 31 and the right optical system 32 are acquired in step S23, after which control goes back to the processing of step S18.

On the other hand, if it is determined that the measured distance is smaller than the threshold value Th2 (step S20: YES), then an image from the left optical system 31 is generated in step S24, and the generated image is displayed on the display 5 in step S25. Then, the two optical paths are switched by the light shield 33, and captured images from the left optical system 31 and the right optical system 32 are acquired in step S26, after which control goes back to the processing of step S4 in FIG. 8.

By thus causing the threshold values to have a hysteresis, the image displayed on the display 5 is prevented from being switched frequently if the measured distance is unstable, so that the endoscopic system 1 can have a better observing capability.

Modification 3

Next, modification 3 of the first embodiment will be described hereinafter.

According to the first embodiment, as illustrated in FIG. 6, the distance is measured each time to determine whether to switch the displayed image. However, for the purpose of carrying out the process of determining whether to switch the displayed image, since it is necessary to switch between the optical paths to acquire captured left and right images and to perform a processing operation for measuring the distance, some processing time needs to be spent. If the endoscopic system 1 is to operate in a live mode, the frame rate is lowered. In order to prevent the frame rate from being lowered, the processing operation for measuring the distance in steps S4 and S5 in FIG. 6 may be carried out once in a plurality of sessions, i.e., in a plurality of frames, and the process of determining whether to switch the displayed image in step S6 in FIG. 6 may be carried out once in a plurality of sessions.

Second Embodiment

Next, a second embodiment will be described hereinafter.

According to the first embodiment, the endoscopic system for performing switching-type stereo measurement to switch between and acquire left and right images has been described. According to a second embodiment, an endoscopic system for performing simultaneous stereo measurement to acquire left and right images simultaneously will be described. The endoscopic system according to the second embodiment has the same overall configuration as the first embodiment.

Figure 10:
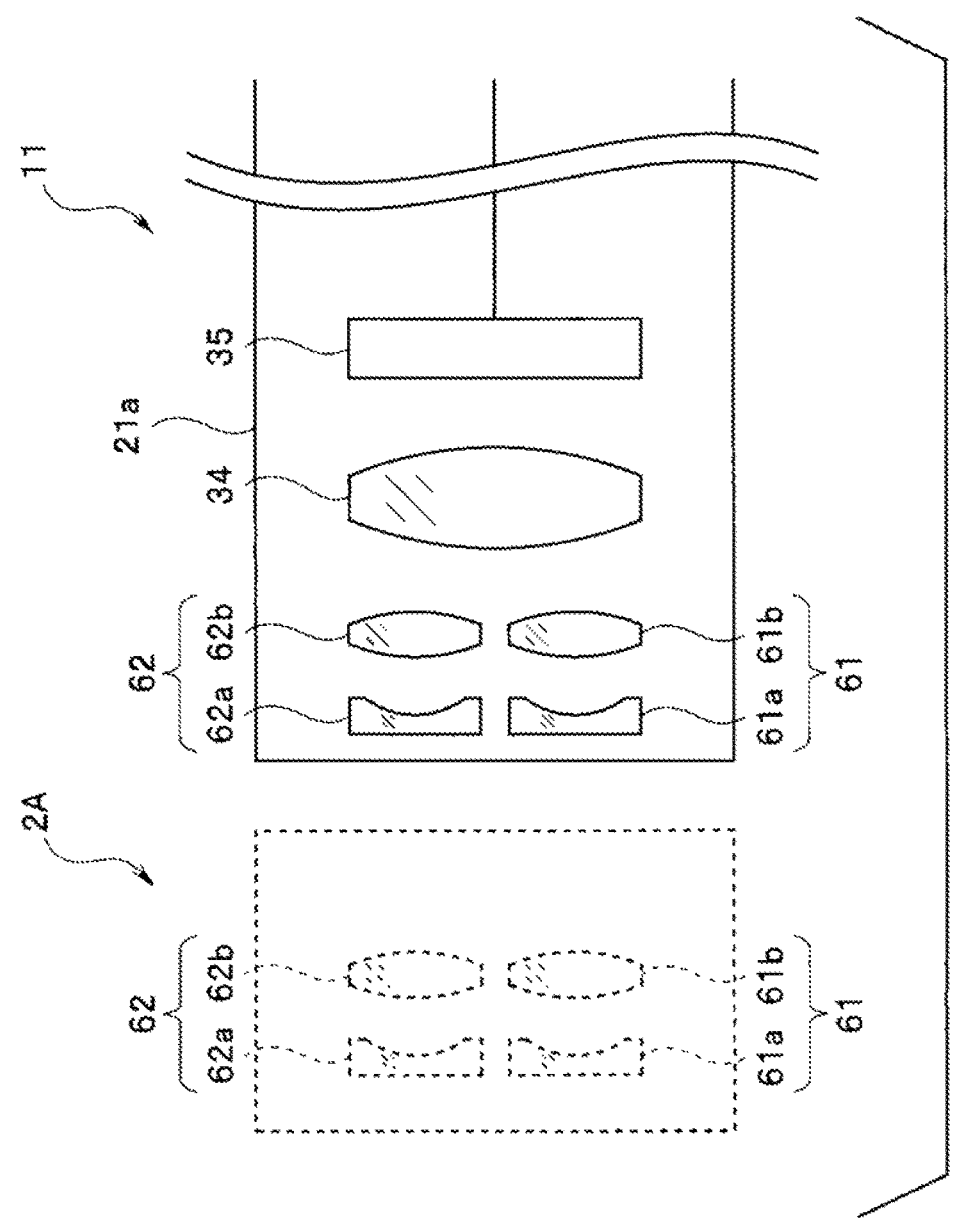
FIG. 10 is a view illustrating a configuration of an optical system in the distal-end portion of an insertion portion according to a second embodiment.

FIG. 10 is a view illustrating a configuration of an optical system in the distal-end portion of an insertion portion according to the second embodiment. Those parts illustrated in FIG. 10 which are identical to those illustrated in FIG. 2 are denoted by identical numeral references, and will not be described in detail hereinafter.

As illustrated in FIG. 10, the insertion portion 11 has a distal-end portion 21a that is free of the light shield 33 in the distal-end portion 21 illustrated in FIG. 2. The distal-end portion 21a has a left optical system 61 and a right optical system 62 instead of the left optical system 31 and the right optical system 32, respectively, illustrated in FIG. 2.

The left optical system 61 includes lenses 61a and 61b. The right optical system 62 includes lenses 62a and 62b. The left optical system 61 and the right optical system 62 are designed to have different focal positions. According to the present embodiment, the left optical system 61 is designed to have its focal position on a near point side, whereas the right optical system 62 is designed to have its focal position on a far point side.

The left optical system 61 and the right optical system 62 are designed to have respective images focused on different areas on the single image capturing device 35 at the same time. In other words, the endoscopic system 1 according to the present embodiment is an apparatus capable of simultaneously acquiring a plurality of images with a parallax. According to the present embodiment, the images from the left optical system 61 and the right optical system 62 are illustrated as being focused on different areas of the single image capturing device 35 at the same time. However, the insertion portion 11 may have two image capturing devices, and the image from the left optical system 61 may be focused on one of the image capturing devices and the image from the right optical system 62 may be focused on the other image capturing device, simultaneously.

The focusing optical system 34 is arranged to focus light that has passed through the two optical paths of the left optical system 61 and the right optical system 62 on the different areas of the image capturing device 35. The image capturing device 35 is disposed in the focal position of the focusing optical system 34, and captures focused images with a parallax from the two optical paths. A captured image signal from the image capturing device 35 is supplied to the main device 4.

The main device 4 selects one of the image from the left optical system 61 and the image from the right optical system 62, which are captured by the image capturing device 35, and displays the selected image on the display 5. Specifically, while a live image, or a moving image, is being observed, the main device 4 selects one of the image from the left optical system 61 and the image from the right optical system 62, which are captured simultaneously, depending on the measured distance, and displays the selected image on the display 5. The display process is the same as the first embodiment.

Specifically, the video signal processor 41 generates an image from the left optical system 61 from the images that are captured simultaneously on the different areas of the image capturing device 35, and displays the generated image on the display 5. The image measurement processor 44 measures the distance up to the cursor 51 set on the display 5, and outputs the measured distance to the proper image determiner 45. The proper image determiner 45 compares the measured distance with the threshold value Th. If the measured distance is larger than the threshold value Th, then the proper image determiner 45 determines that the image from the right optical system 62 is a proper image, and if the measured distance is equal to or smaller than the threshold value Th, then the proper image determiner 45 determines that the image from the left optical system 61 is a proper image. The proper image determiner 45 outputs the determined result to the video signal processor 41. The video signal processor 41 outputs a better-focused image of the left and right images to the display 5 based on the determined result from the proper image determiner 45.

As a consequence, the endoscopic system 1 according to the present embodiment is thus capable of displaying better-focused images without causing an increase in the burden on the CPU and making the distal-end portion 21a larger in diameter, as with the endoscopic system 1 according to the first embodiment.

Modification 1

Next, modification 1 of the second embodiment will be described hereinafter.

According to the second embodiment, while a live image, or a moving image, is being observed, the main device 4 selects one of the image from the left optical system 61 and the image from the right optical system 62, which are captured simultaneously, depending on the measured distance, and displays the selected image.

According to the modification, however, while a live image, or a moving image, is being observed, the main device 4 simultaneously displays the image from the left optical system 61 and the image from the right optical system 62 on the display 5. In the event of a freeze instruction, the main device 4 selects one of the image from the left optical system 61 and the image from the right optical system 62, which are captured simultaneously, depending on the measured distance, and displays the selected image on the display 5.

Figure 11A:
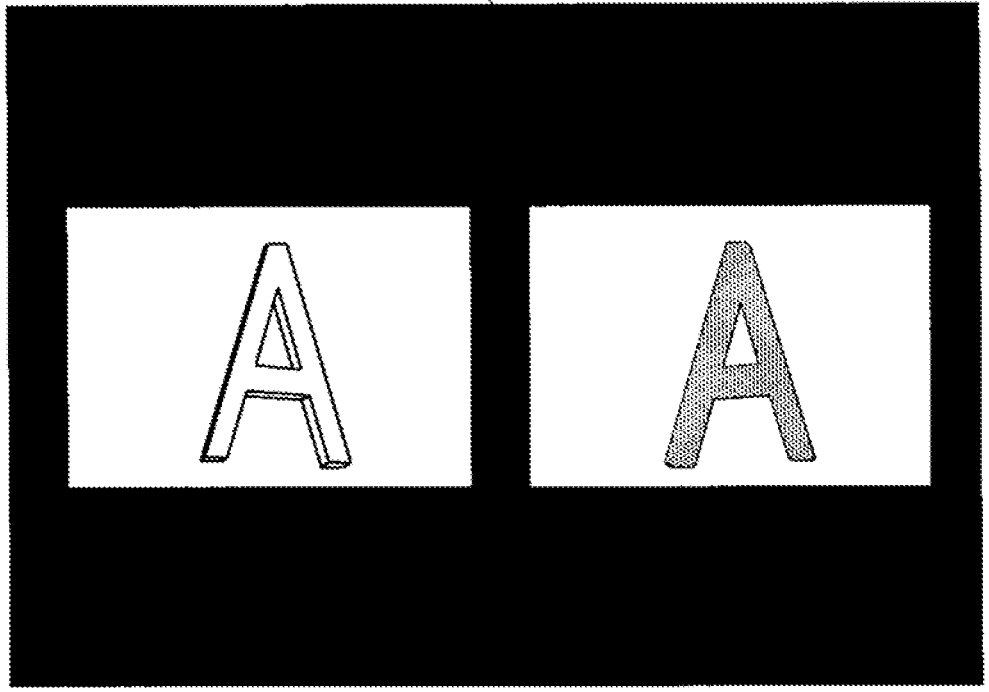
FIG. 11A is a diagram illustrating an example of an image displayed on a display.
Figure 11B:
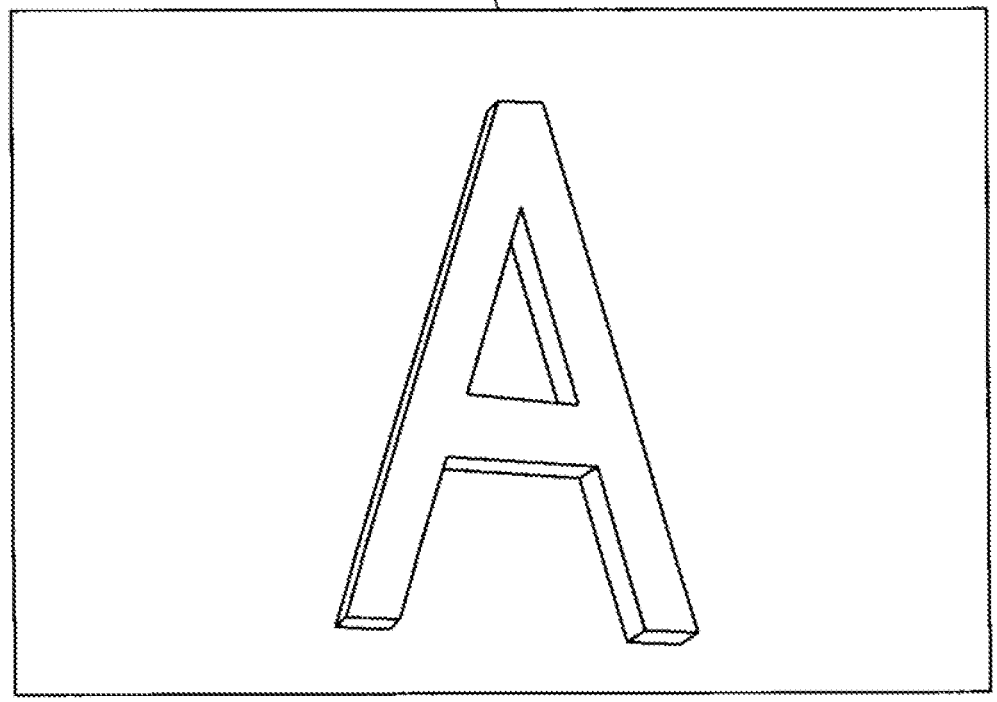
FIG. 11B is a diagram illustrating an example of an image displayed on the display.

FIGS. 11A and 11B are diagrams illustrating examples of images displayed on the display 5. While a live image is being observed, the left and right images from the left optical system 61 and the right optical system 62 are displayed, as illustrated in FIG. 11A. In the event of a freeze instruction, a better-focused one of the left and right images acquired by the left optical system 61 and the right optical system 62 is displayed, as illustrated in FIG. 11B. The freeze instruction can be given by the user using a freeze button or the like, not illustrated, disposed on the manipulator 12.

Figure 12:
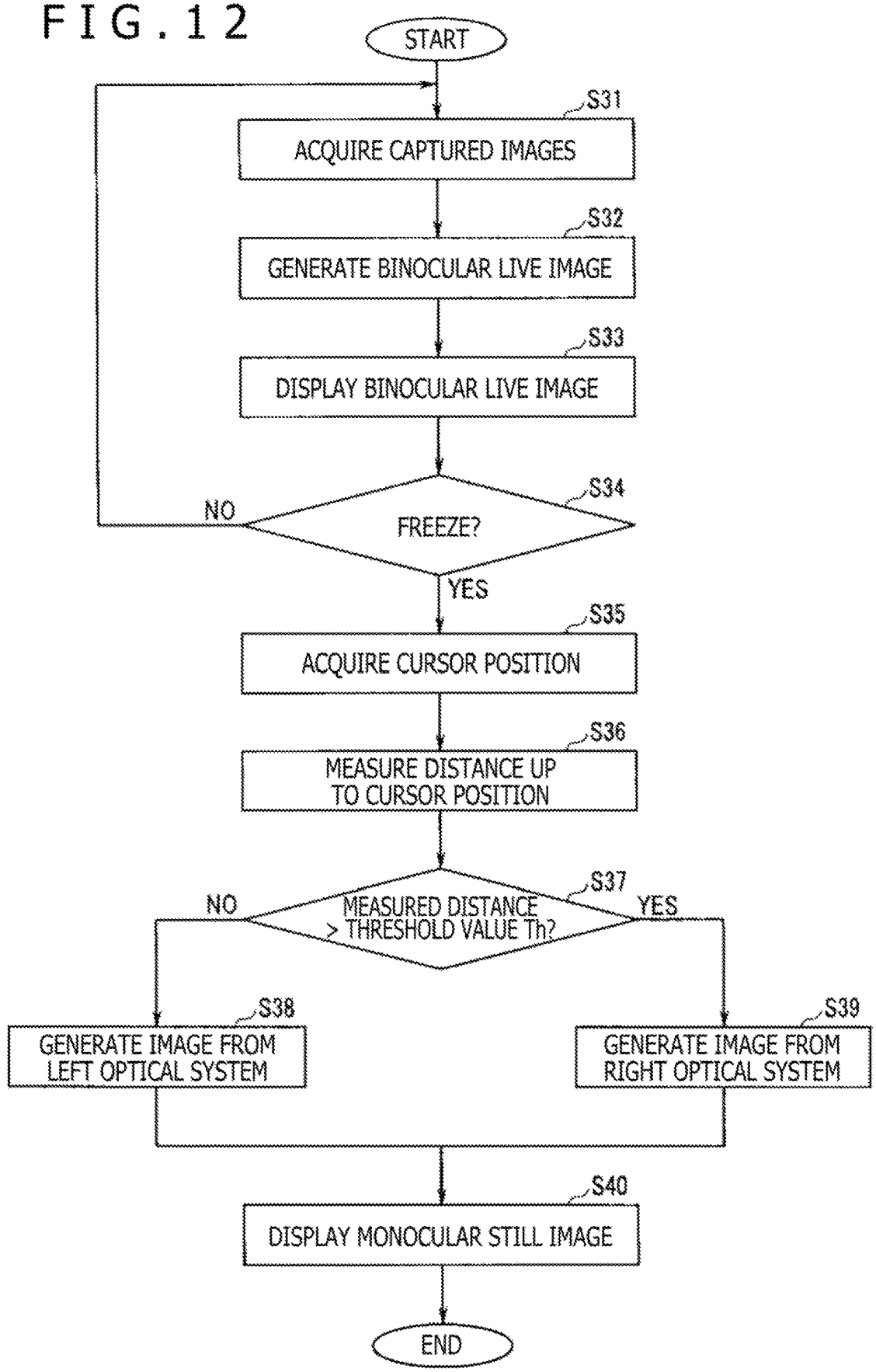
FIG. 12 is a flowchart illustrating an example of a display process for displaying a proper image in the event of a freeze instruction.

Next, a display process for displaying a proper image in the event of a freeze instruction will be described hereinafter. FIG. 12 is a flowchart illustrating an example of the display process for displaying a proper image in the event of a freeze instruction.

When the endoscopic system 1 is activated, captured images from the left optical system 61 and the right optical system 62 are acquired in step S31, a binocular live image is generated from the captured images from the left optical system 61 and the right optical system 62 in step S32, and the generated binocular live image is displayed on the display 5 in step S33.

Then, it is determined whether there is a freeze instruction from the user or not in step S34. The user gives a freeze instruction using a freeze button or the like disposed on the manipulator 12, for example. If it is determined that there is no freeze instruction (step S34: NO), control goes back to step S31, and the same processing is repeated. On the other hand, if it is determined that there is a freeze instruction (step S34: YES), a cursor position is acquired in step S35. The cursor position is set on the screen of the display 5 by the user using the manipulator 12.

The distance up to the cursor position on the screen is measured according to stereo measurement in step S36. It is determined whether the measured distance is larger than the threshold value Th or not in step S37. If it is determined that the measured distance is not larger than the threshold value Th (step S37: NO), i.e., if it is determined that the measured distance is equal to or smaller than the threshold value Th, then an image from the left optical system 61 is generated in step S38. On the other hand, if it is determined that the measured distance is larger than the threshold value Th (step S37: YES), then an image from the right optical system 62 is generated in step S39.

Finally, one of the image from the left optical system 61 that has been generated in step S38 and the image from the right optical system 62 that has been generated in step S39 is displayed as a monocular still image on the display 5 in step S40, after which the processing is ended.

As described hereinbefore, while on a live image, both images from the right optical system and the left optical system which have different focal positions are displayed, so that the near point side can be observed with the left image and the far point side can be observed with the right image, allowing the field of depth to be increased when the live image is observed.

On the other hand, in the event of a freeze instruction from the user to display a still image, a better-focused one of the left image and the right image is displayed thereby to display an image suitable for a measurement function on a still image. For measuring a flaw on an object to be inspected, for example, a point where three-dimensional measurement is to be performed on a still image may be designated by the user, so that an accurate measuring point can be designated using a better-focused image with good observability. Furthermore, only one of the images may be displayed as a still image for better visibility to make it possible to designate a more accurate measuring point and to reduce measurement errors.

Modification 2

Next, modification 2 of the second embodiment will be described hereinafter.

According to modification 2, an endoscopic system for displaying a proper image in highlight will be illustrated hereinafter. According to modification 2, a process of displaying a proper image is different from the display process according to the second embodiment.

Figure 13A:
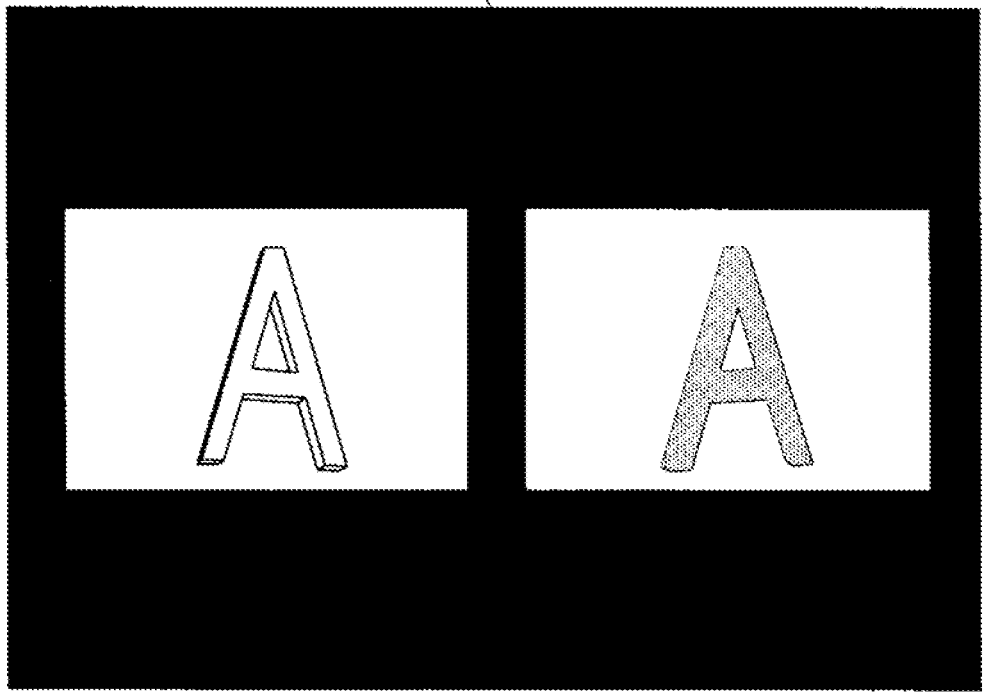
FIG. 13A is a diagram illustrating an example of highlight display.
Figure 13B:
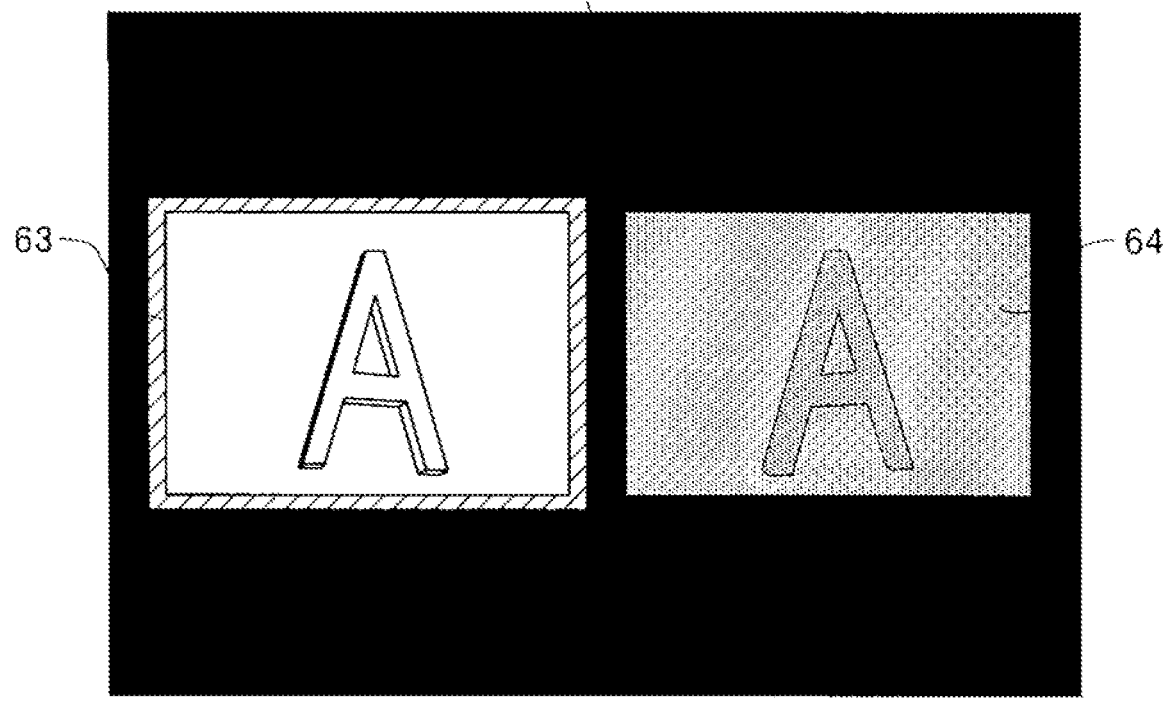
FIG. 13B is a diagram illustrating the example of highlight display.
Figure 14A:
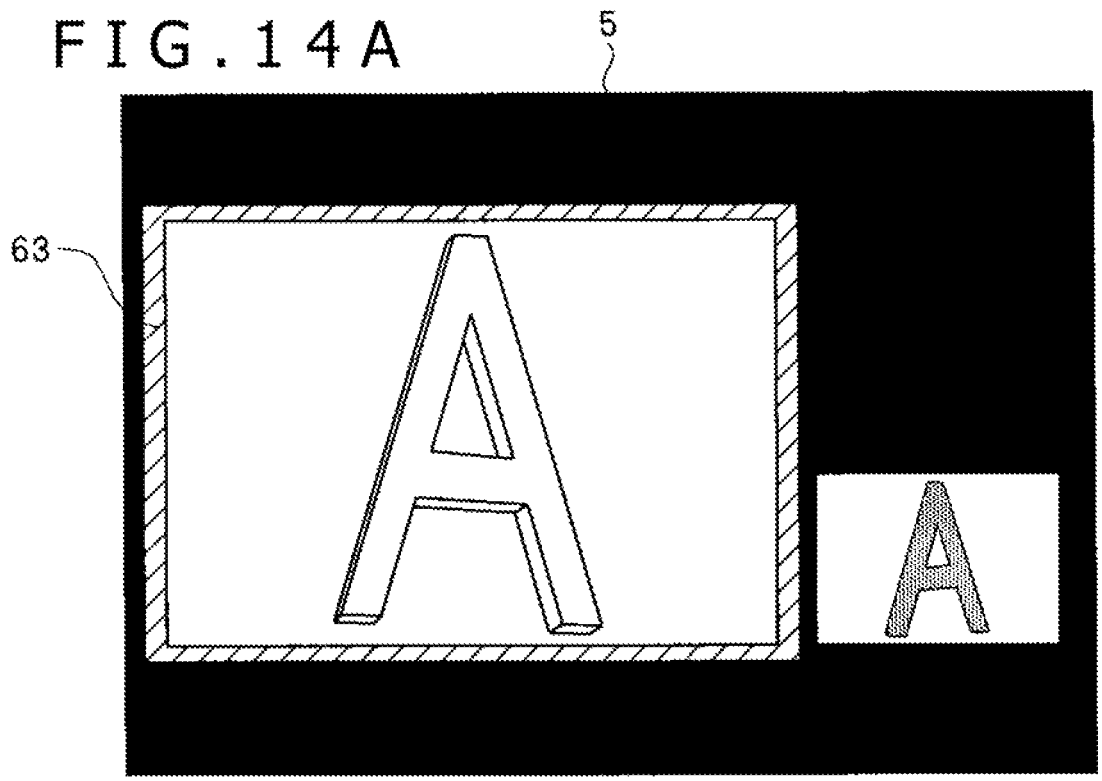
FIG. 14A is a diagram illustrating another example of highlight display.
Figure 14B:
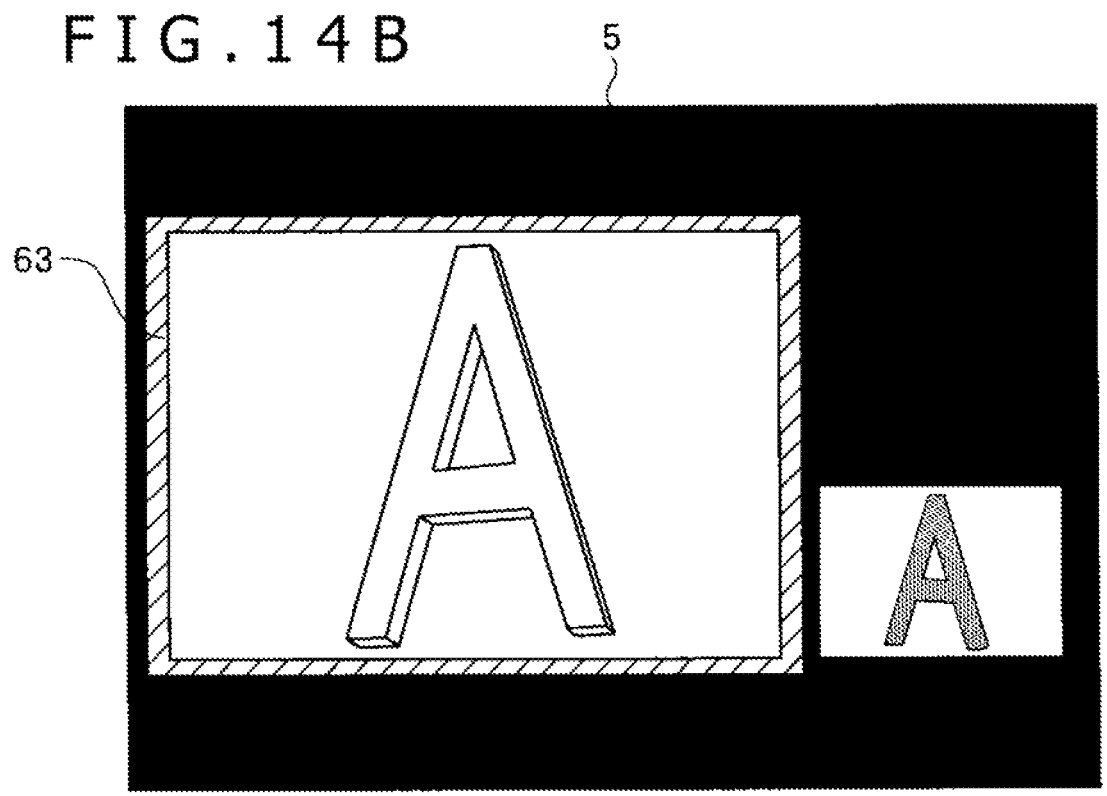
FIG. 14B is a diagram illustrating the other example of highlight display.

FIGS. 13A and 13B are diagrams illustrating an example of highlight display, and FIGS. 14A and 14B are diagrams illustrating another example of highlight display.

As illustrated in FIG. 13A, while a live image is being displayed, both the image from the left optical system 61 and the image from the right optical system 62 that are captured from the different areas of the single image capturing device 35 are displayed on the display 5. The proper image determiner 45 determines a proper image based on the measured distance from the image measurement processor 44, and outputs the determined result to the video signal processor 41. The process of determining a proper image is the same as the second embodiment. Based on the determined result from the proper image determiner 45, the video signal processor 41 performs highlight display by surrounding the image determined as the proper image with a frame 63 as illustrated in FIG. 13B. Furthermore, the video signal determiner 41 may gray out the image determined as not the proper image as indicated by numeral reference 64, indicating to the user that the image is not the proper image.

Moreover, as illustrated in FIG. 14A, the video signal processor 41 may display the image determined as the proper image in a scaled-up size. In the example illustrated in FIG. 14A, the left image is determined as the proper image and displayed in a scaled-up size. At this time, as with the example illustrated in FIG. 13B, the image determined as the proper image may be surrounded by the frame 63 for highlight display. With this arrangement, an image that is in better focus in an area that the user is interested in can be observed as a larger image for better observability.

Furthermore, when the proper image changes from the left image to the right image or from the right image to the left image, the video signal processor 41 may keep the display position of the proper image unchanged. For example, the left image is displayed in a scaled-up size as the proper image in FIG. 14A. If the proper image determiner 45 determines that the proper image has changed from the left image to the right image depending on the measured distance, then the video signal processor 41 displays, as illustrated in FIG. 14, the right image newly determined as the proper image in the display position where the left image has been displayed as the proper image. The proper image is thus displayed at all times in the same area within the screen of the display 5, allowing the user to perform an inspection by observing the same area within the screen.

The steps in the flowcharts in the present description may be changed as to the order of execution, may be carried out simultaneously, or may be carried out in a different order in each cycle of execution, unless such alternatives have adverse effects on the steps.

In sum, the disclosed technology is directed to an endoscopic system comprises a first optical system having a first focal position and forming a first image of a subject. A second optical system having a second focal position that is different from the first focal position and forming a second image the subject. An image capturing device having an image capturing surface configured to capture the first image and the second image. A display device displays the first image or the second image being captured by the image capturing device. A processor is configured to compare a position of the subject in a part of an area displayed on the display device with at least one threshold value being established between the first focal position and the second focal position and output a determined result. The part of the area is set or changed by a user with a cursor on the image displayed by the display device. Then, switch to the first image or the second image based on the determined result and control the display device for displaying the first image or the second image.

The first image and the second image are formed on a same image capturing area of the image capturing surface. The endoscopic system further comprises an optical path switcher switches between a first optical path of the first optical system and a second optical path of the second optical system on a time-division basis. The processor is configured to acquire the first image and the second image on the time-division basis while the first optical system and the second optical system are being switched by the optical path switcher. The first image and the second image are formed on different image capturing areas of the image capturing surface. The processor is configured to acquire the first image and the second image on the different image capturing areas at a same time. The processor is configured to calculate an amount of light, calculate the position of the subject in the part of the area displayed on the display device using the amount of light applied to the image capturing surface, and to compare the position of the subject with the at least one threshold value established between the first focal position and the second focal position.

The processor is configured to calculate an area feature quantity, calculate the position of the subject in the part of the area displayed on the display device using the area feature quantity of the first image or the second image, and to compare the position of the subject with the at least one threshold value established between the first focal position and the second focal position. The processor is configured to control the display device for displaying the first image or the second image in highlight based on the determined result. when the image is displayed on the display device changes from the first image to the second image or from the second image to the first image and in which the processor is configured to control a display position of the image displayed in highlight to remain in a same position. Each of the first optical system and the second optical system includes a parallax with respect to one another. The processor is configured to measure a distance up to the position of the subject in the part of the area by performing stereo measurement on the first image and the second image and outputting a measured distance. The processor is configured to calculate the position of the subject in the part of the area displayed on the display device using the measured distance and to compare the position of the subject with the at least one threshold value established between the first focal position and the second focal position.

The processor is configured to measure the subject on the image displayed on the display device. The processor is configured to generate a deblurred image by deblurring either the first image or the second image and to perform the stereo measurement using the deblurred image and other image which is not deblurred. The processor is configured to generate a blurred image by blurring either the first image or the second image and to perform the stereo measurement using the blurred image and other image which is not blurred. The processor is configured to generate a deblurred image by deblurring either the first image or the second image, to generate a blurred image by blurring other image of the first image or the second image and to perform the stereo measurement using the deblurred image and the blurred image. The processor is configured to determine the position of the subject in the part of the area displayed on the display device, to calculate the position of the subject, and if the determined result remains the same successively in a plurality of times, switch to the first image or the second image, and control the display device for displaying the image. The predetermined threshold value has a hysteresis. The predetermined threshold value is established intermediate between the first focal position and the second focal position. While a live image is being observed, the processor is configured to control the display device for displaying the first image and the second image, and in an event of a freeze instruction, the processor is configured to control the display device for displaying the first image or the second image captured entirely on the display device based on the determined result. The first focal position of the first optical system and the second focal position of the second optical system are different from each other due to a variation in a manufacturing process therefor.

An endoscopic system comprises a first optical system having a first focal position and configured to form a first image of a subject. A second optical system having a second focal position that is different from the first focal position and is configured to form a second image the subject. Each of the first optical system and the second optical system includes a parallax with respect to one another. An image capturing device having an image capturing surface and is configured to capture the respective first image and the second image. A display device displays the first image or the second image being captured by the image capturing device. A processor is configured to compare a position of the subject in a part of an area displayed on the display device with at least one threshold value being established between the first focal position and the second focal position and output a determined result. Switch to the first image or the second image based on the determined result and control the display device for displaying the first image or the second image and to measure a distance up to the position of the subject in the part of the area by performing stereo measurement on the first image and the second image and output a measured distance.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. An endoscopic system comprising:
a first optical system having a first focal position and forming a first image of a subject;
a second optical system having a second focal position that is different from the first focal position and forming a second image of the subject;
an image sensor having an image capturing surface and configured to capture the first image and the second image;
a display configured to display either one of the first image or the second image captured by the image sensor; and
a processor comprising hardware, the processor being configured to:
compare a position of the subject in a part of an area displayed on the display device with at least one threshold position value, and output a determined result based on the comparison; and
select, based on the determined result, one of the first image or the second image to be displayed on the display and control, based on a selection result, the display for displaying only the selected one of the first image or the second image.

2. The endoscopic system of claim 1, wherein the part of the area is set or changed by a user with a cursor on the image displayed by the display.

3. The endoscopic system of claim 1, wherein the first image and the second image are formed on a same image capturing area of the image sensor and wherein the endoscopic system further comprising:
an optical path switch configured to switch between a first optical path of the first optical system and a second optical path of the second optical system on a time-division basis; wherein
the processor is configured to acquire the first image and the second image on the time-division basis while the first optical system and the second optical system are being switched by the optical path switch.

4. The endoscopic system of claim 1, wherein the first image and the second image are formed on different image capturing areas of the image sensor; and
wherein the processor is configured to acquire the first image and the second image on the different image capturing areas at a same time.

5. The endoscopic system of claim 1, wherein the processor is configured to:
calculate an amount of light;
calculate the position of the subject in the part of the area displayed on the display using the amount of light applied to the image capturing surface, and
compare the position of the subject with the at least one threshold position value established between the first focal position and the second focal position.

6. The endoscopic system of claim 1, wherein the processor is configured to:
calculate an area feature quantity;
calculate the position of the subject in the part of the area displayed on the display using the area feature quantity of the first image or the second image, and
compare the position of the subject with the at least one threshold position value established between the first focal position and the second focal position.

7. The endoscopic system of claim 1, wherein the processor is configured to control the display for displaying the first image or the second image in highlight based on the determined result.

8. The endoscopic system of claim 7, wherein when the image displayed on the display changes from the first image to the second image or from the second image to the first image and wherein the processor is configured to control a display position of the image displayed in highlight to remain in a same position.

9. The endoscopic system of claim 1, wherein the processor is configured to
determine the position of the subject in the part of the area displayed on the display,
calculate the position of the subject, and if the determined result remains the same successively in a plurality of times,
switch to the first image or the second image, and
control the display device for displaying the image.

10. The endoscopic system of claim 1, wherein the predetermined threshold position value has a hysteresis.

11. The endoscopic system of claim 1, wherein the predetermined threshold position value is established intermediate between the first focal position and the second focal position.

12. The endoscopic system of claim 1, wherein while a live image is being observed, the processor is configured to control the display for displaying the first image and the second image, and in an event of a freeze instruction, the processor is configured to control the display for displaying the first image or the second image captured entirely on the display based on the determined result.

13. The endoscopic system of claim 1, wherein the first focal position of the first optical system and the second focal position of the second optical system are different from each other due to a variation in a manufacturing process therefor.

14. The endoscopic system of claim 1, wherein the threshold position value being between the first focal position and the second focal position.

15. The endoscopic system of claim 14, wherein each of the first optical system and the second optical system includes a parallax with respect to one another and wherein
the processor is configured to measure a distance up to the position of the subject in the part of the area by performing stereo measurement on the first image and the second image and outputting a measured distance.

16. The endoscopic system of claim 15, wherein the processor is configured to
calculate the position of the subject in the part of the area displayed on the display using the measured distance, and compare the position of the subject with the at least one threshold position value established between the first focal position and the second focal position.

17. The endoscopic system of claim 15, wherein the processor is configured to measure the subject on the image displayed on the display.

18. The endoscopic system of claim 15, wherein the processor is configured to
   generate a deblurred image by deblurring either the first image or the second image, and
   perform the stereo measurement using the deblurred image and an other of the first image and the second image which is not deblurred.

19. The endoscopic system of claim 15, wherein the processor is configured to generate a blurred image by blurring either the first image or the second image,
   perform the stereo measurement using the blurred image and an other of the first image and the second image which is not blurred.

20. The endoscopic system of claim 15, wherein the processor is configured to
   generate a deblurred image by deblurring either the first image or the second image;
   generate a blurred image by blurring an other of the first image or the second image; and
   perform the stereo measurement using the deblurred image and the blurred image.

21. An endoscopic system comprising:
   a first optical system having a first focal position and configured to form a first image of a subject;
   a second optical system having a second focal position that is different from the first focal position and configured to form a second image of the subject wherein each of the first optical system and the second optical system includes a parallax with respect to one another;
   an image sensor having an image capturing surface and configured to capture the respective first image and the second image;
   a display configured to display either one of the first image or the second image captured by the image sensor; and
   a processor comprising hardware, the processor being configured to:
      compare a position of the subject in a part of an area displayed on the display device with at least one threshold position value, the threshold position value being between the first focal position and the second focal position and output a determined result based on the comparison;
      select, based on the determined result, one of the first image or the second image to be displayed on the display and control, based on a selection result, the display for displaying only the selected one of the first image or the second image; and
      measure a distance up to the position of the subject in the part of the area by performing stereo measurement on the first image and the second image and output a measured distance.

* * * * *